US 11,771,597 B2

(12) United States Patent
Bacher et al.

(10) Patent No.: US 11,771,597 B2
(45) Date of Patent: Oct. 3, 2023

(54) MULTIPLE-INPUT-COUPLED ILLUMINATED MULTI-SPOT LASER PROBE

(71) Applicant: Alcon Inc., Fribourg (CH)

(72) Inventors: Gerald David Bacher, Carlsbad, CA (US); Mark Harrison Farley, Laguna Hills, CA (US); Alireza Mirsepassi, Irvine, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 1191 days.

(21) Appl. No.: 16/217,383

(22) Filed: Dec. 12, 2018

(65) Prior Publication Data

US 2019/0175407 A1    Jun. 13, 2019

Related U.S. Application Data

(60) Provisional application No. 62/630,865, filed on Feb. 15, 2018, provisional application No. 62/622,299, (Continued)

(51) Int. Cl.
*A61F 9/008* (2006.01)
*A61B 18/22* (2006.01)
(Continued)

(52) U.S. Cl.
CPC .......... *A61F 9/00821* (2013.01); *A61B 18/22* (2013.01); *A61B 18/24* (2013.01); *A61B 90/30* (2016.02); *A61F 9/008* (2013.01); *A61F 9/00823* (2013.01); *G02B 6/3843* (2013.01); *G02B 6/3851* (2013.01); *G02B 6/3885* (2013.01); *A61B 2018/00779* (2013.01); *A61B 2018/208* (2013.01); *A61B 2018/2025* (2013.01); *A61B 2018/2065* (2013.01); *A61B 2018/2211* (2013.01); *A61B 2018/2255* (2013.01); *A61B 2018/2266* (2013.01); *A61B 2018/2294* (2013.01);
(Continued)

(58) Field of Classification Search
None
See application file for complete search history.

(56) References Cited

U.S. PATENT DOCUMENTS

| 5,199,431 A | 4/1993 | Kittrell |
| 5,496,305 A | 3/1996 | Kittrell |

(Continued)

FOREIGN PATENT DOCUMENTS

| JP | H02297355 A | 12/1990 |
| JP | A1994014936 A | 1/1994 |

(Continued)

OTHER PUBLICATIONS

Notice of Reasons of Rejection for Japanese Patent Application No. 2020-531700, dated Jan. 10, 2023, 8 pages.

*Primary Examiner* — James M Kish
*Assistant Examiner* — Jessica L Mullins
(74) *Attorney, Agent, or Firm* — Patterson + Sheridan, LLP

(57) ABSTRACT

Systems and methods for creating multi-spot laser light beams, multiplexing an illumination light and the multi-spot laser light beams, delivering the multiplexed light to a surgical handpiece via a multi-core optical fiber cable, and delivering the multiplexed light onto patient anatomy.

16 Claims, 19 Drawing Sheets

Related U.S. Application Data filed on Jan. 26, 2018, provisional application No. 62/598,653, filed on Dec. 14, 2017, provisional application No. 62/597,550, filed on Dec. 12, 2017.

(51) Int. Cl.

| | | |
|---|---|---|
| *G02B 6/38* | (2006.01) | |
| *A61B 90/30* | (2016.01) | |
| *A61B 18/24* | (2006.01) | |
| *G02B 6/02* | (2006.01) | |
| *G02B 6/42* | (2006.01) | |
| *A61B 18/00* | (2006.01) | |
| *A61B 18/20* | (2006.01) | |

(52) U.S. Cl.
CPC .............. *A61B 2090/306* (2016.02); *A61F 2009/00863* (2013.01); *G02B 6/02042* (2013.01); *G02B 6/4206* (2013.01)

(56) References Cited

U.S. PATENT DOCUMENTS

| | | | |
|---|---|---|---|
| 5,625,638 A | 4/1997 | Trost | |
| 5,693,043 A | 12/1997 | Kittrell | |
| 5,815,626 A * | 9/1998 | Kuba | B23K 26/0648 385/38 |
| 5,921,981 A | 7/1999 | Bahmanyar et al. | |
| 6,066,128 A | 5/2000 | Bahmanyar et al. | |
| 6,096,028 A | 8/2000 | Bahmanyar et al. | |
| 6,893,432 B2 | 5/2005 | Intintoli et al. | |
| 7,189,226 B2 | 3/2007 | Auld et al. | |
| 7,302,142 B2 | 11/2007 | Conde | |
| 7,448,995 B2 | 11/2008 | Wiklof | |
| 7,566,173 B2 | 7/2009 | Auld et al. | |
| 8,398,240 B2 | 3/2013 | Smith | |
| 8,488,930 B2 | 7/2013 | Papac | |
| 8,498,506 B2 | 7/2013 | Smith | |
| 8,561,280 B2 | 10/2013 | Diao et al. | |
| 8,571,364 B2 | 10/2013 | Smith | |
| 8,764,261 B2 | 7/2014 | Smith | |
| 8,903,475 B2 | 12/2014 | Brennan et al. | |
| 8,939,964 B2 | 1/2015 | Smith | |
| 8,951,244 B2 | 2/2015 | Smith | |
| 8,968,347 B2 | 3/2015 | McCollam | |
| 9,055,885 B2 | 6/2015 | Horvath | |
| 9,107,730 B2 | 8/2015 | Huculak et al. | |
| 9,211,214 B2 | 12/2015 | Rubinchik | |
| 9,308,128 B2 | 4/2016 | Smith | |
| 9,364,982 B2 | 6/2016 | Schaller | |
| 9,387,040 B2 | 7/2016 | Smith | |
| 9,402,643 B2 | 8/2016 | Auld | |
| 9,681,793 B2 | 6/2017 | Artsyukhovich | |
| 10,012,800 B2 | 7/2018 | Diao | |
| 10,016,302 B2 | 7/2018 | Shazly | |
| 10,111,778 B2 | 10/2018 | Smith | |
| 10,245,181 B2 | 4/2019 | Diao | |
| 10,433,718 B2 | 10/2019 | Liolios | |
| 10,441,157 B2 | 10/2019 | Smith | |
| 2002/0045811 A1 | 4/2002 | Kittrell | |
| 2004/0236183 A1 | 11/2004 | Durell | |
| 2006/0184162 A1 | 8/2006 | Smith | |
| 2007/0282312 A1* | 12/2007 | Rathjen | A61F 9/00825 606/4 |
| 2008/0051770 A1 | 2/2008 | Scheller et al. | |
| 2008/0177257 A1 | 7/2008 | Smith et al. | |
| 2008/0215041 A1 | 9/2008 | Zemmouri | |
| 2008/0243108 A1 | 10/2008 | Murakami | |
| 2009/0270850 A1 | 10/2009 | Zhou | |
| 2009/0287196 A1 | 11/2009 | Zelickson | |
| 2009/0287197 A1 | 11/2009 | Hanley | |
| 2010/0027943 A1 | 2/2010 | Armani | |
| 2010/0261961 A1 | 10/2010 | Scott | |
| 2011/0122366 A1 | 5/2011 | Smith | |
| 2011/0144627 A1 | 6/2011 | Smith | |
| 2012/0191078 A1 | 7/2012 | Yadlowsky | |
| 2013/0097843 A1 | 4/2013 | Diao et al. | |
| 2013/0150839 A1 | 6/2013 | Smith | |
| 2014/0180264 A1* | 6/2014 | Diao | A61F 9/00821 606/4 |
| 2014/0194862 A1 | 7/2014 | Smith et al. | |
| 2014/0200566 A1 | 7/2014 | Smith | |
| 2014/0250668 A1 | 9/2014 | Smith | |
| 2015/0351629 A1 | 12/2015 | Wheatley | |
| 2015/0366432 A1 | 12/2015 | Artsyukhovich | |
| 2016/0025933 A1* | 1/2016 | Benisty | G02B 6/4296 385/18 |
| 2016/0178844 A1 | 6/2016 | Griffin | |
| 2018/0055596 A1 | 3/2018 | Johnson | |
| 2018/0243136 A1 | 8/2018 | Diao | |
| 2018/0243137 A1 | 8/2018 | Diao | |
| 2018/0333304 A1 | 11/2018 | Diao | |
| 2018/0344528 A1 | 12/2018 | Farley | |
| 2019/0142544 A1 | 5/2019 | Horn | |
| 2019/0175217 A1 | 6/2019 | Cook | |
| 2019/0175273 A1 | 6/2019 | Cook | |
| 2019/0175300 A1 | 6/2019 | Horn | |
| 2019/0175404 A1 | 6/2019 | Cook | |
| 2019/0175405 A1 | 6/2019 | Diao | |
| 2019/0175406 A1 | 6/2019 | Cook | |
| 2019/0175408 A1 | 6/2019 | Diao | |
| 2019/0209372 A1 | 7/2019 | Farley | |
| 2019/0307527 A1 | 10/2019 | Grueebler | |
| 2019/0365569 A1 | 12/2019 | Skovgaard | |
| 2020/0107960 A1 | 4/2020 | Bacher et al. | |

FOREIGN PATENT DOCUMENTS

| | | | |
|---|---|---|---|
| JP | 2010158331 A | 7/2010 | |
| JP | 201348864 A | 3/2013 | |
| JP | 2013048864 * | 3/2013 | |
| JP | 2015163193 A | 9/2015 | |
| WO | WO9208427 A2 | 9/1992 | |
| WO | WO-0137769 A1 * | 5/2001 | A61F 9/00802 |
| WO | WO2001037769 A1 | 5/2001 | |
| WO | WO2008024848 A2 | 2/2008 | |
| WO | WO2018113887 A2 | 6/2018 | |

* cited by examiner

Proximal Interface

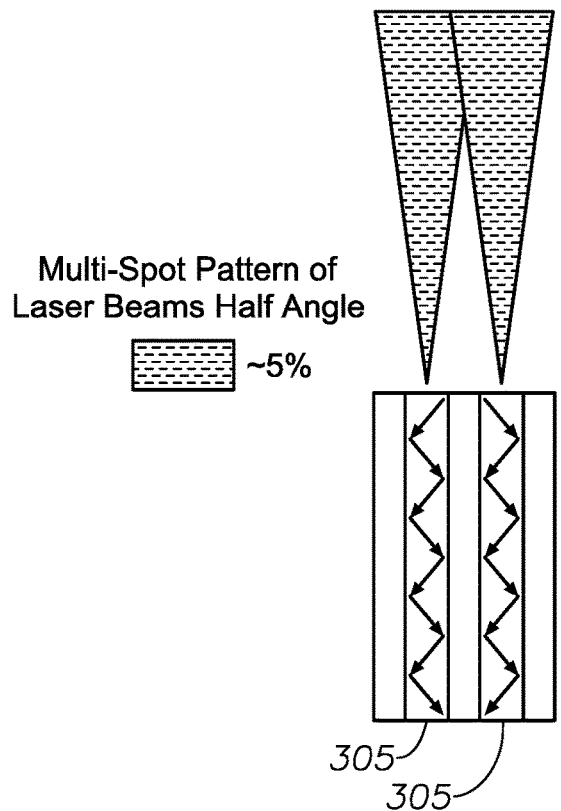
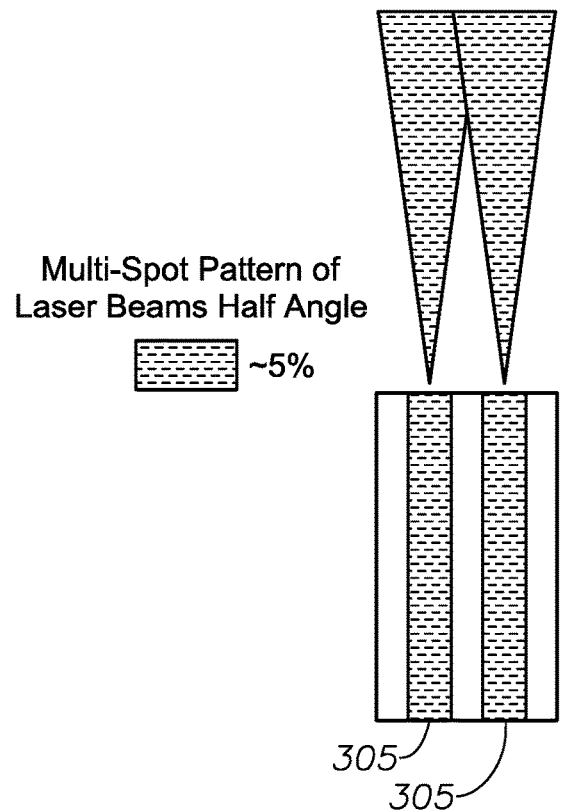
FIG. 3G
FIG. 3H
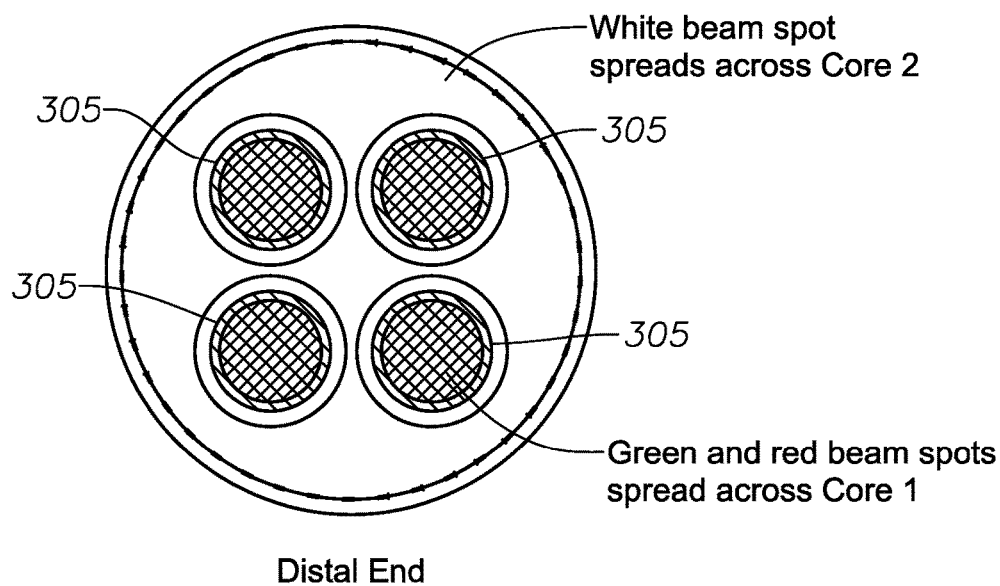
Distal End
FIG. 3I

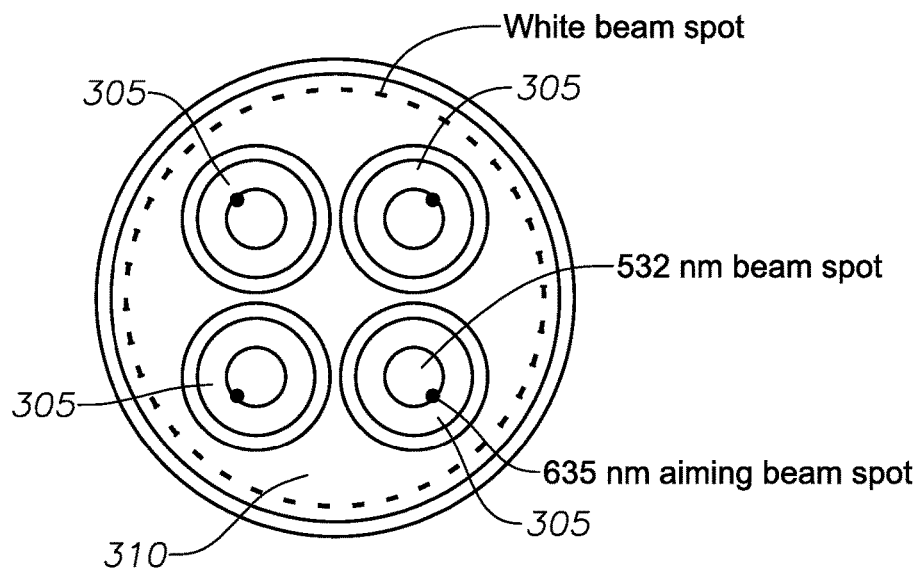
FIG. 3J
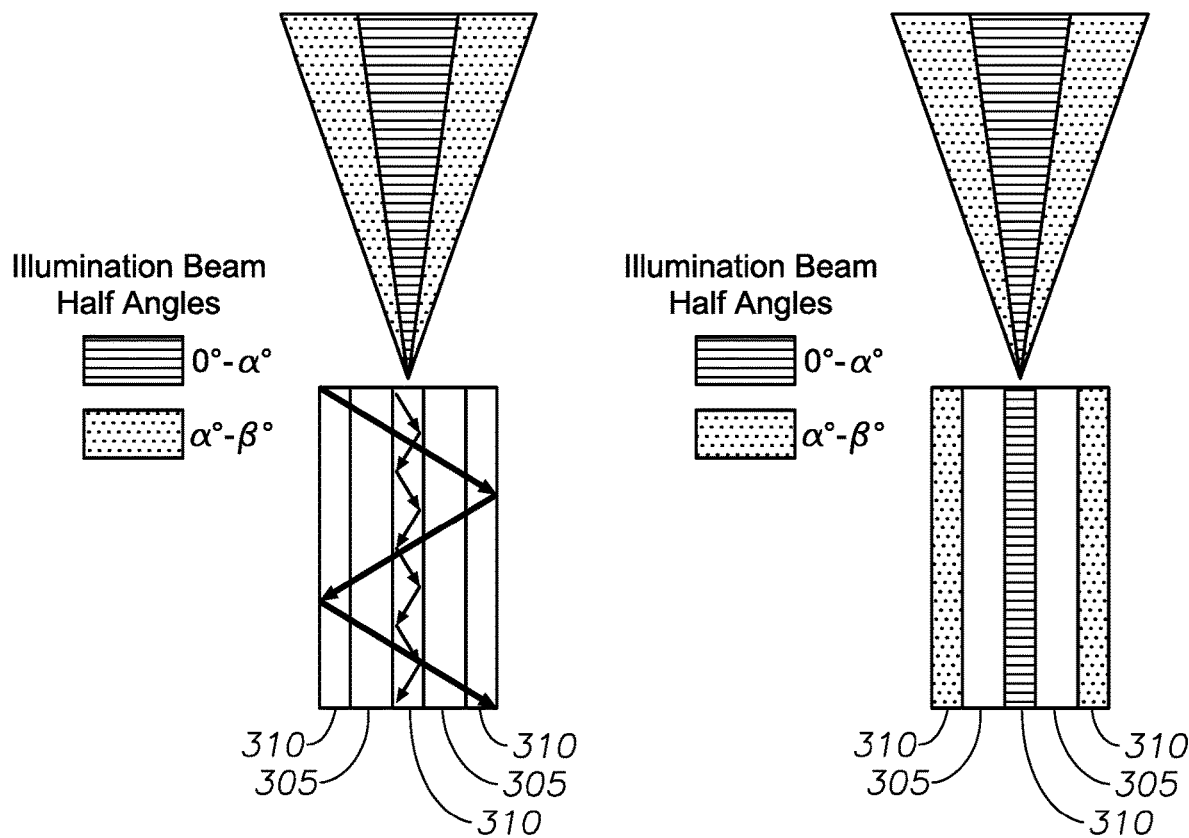
FIG. 3K
FIG. 3L

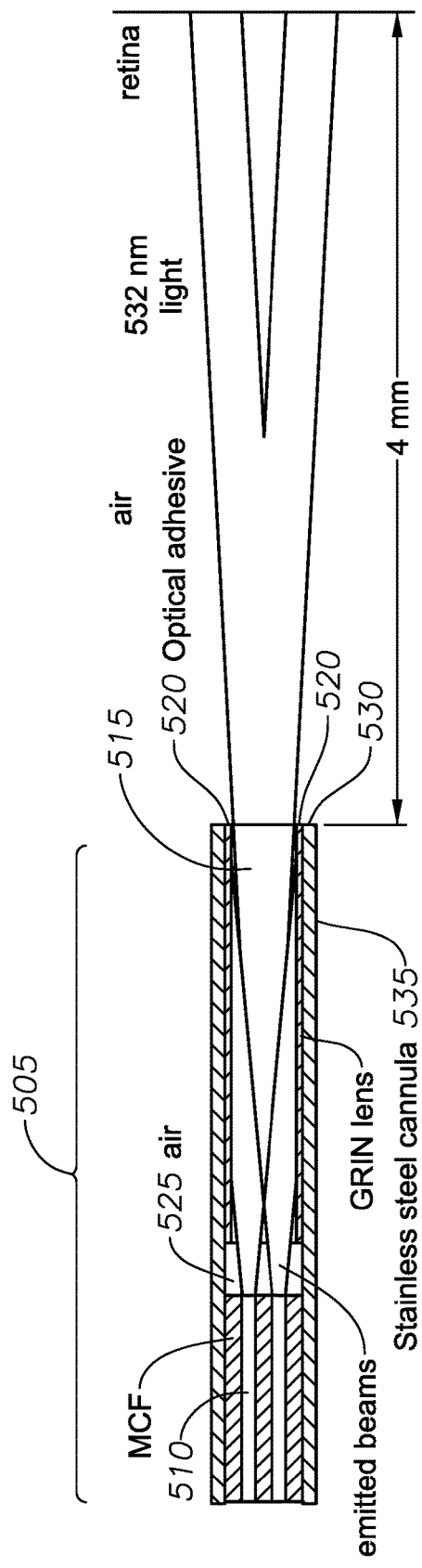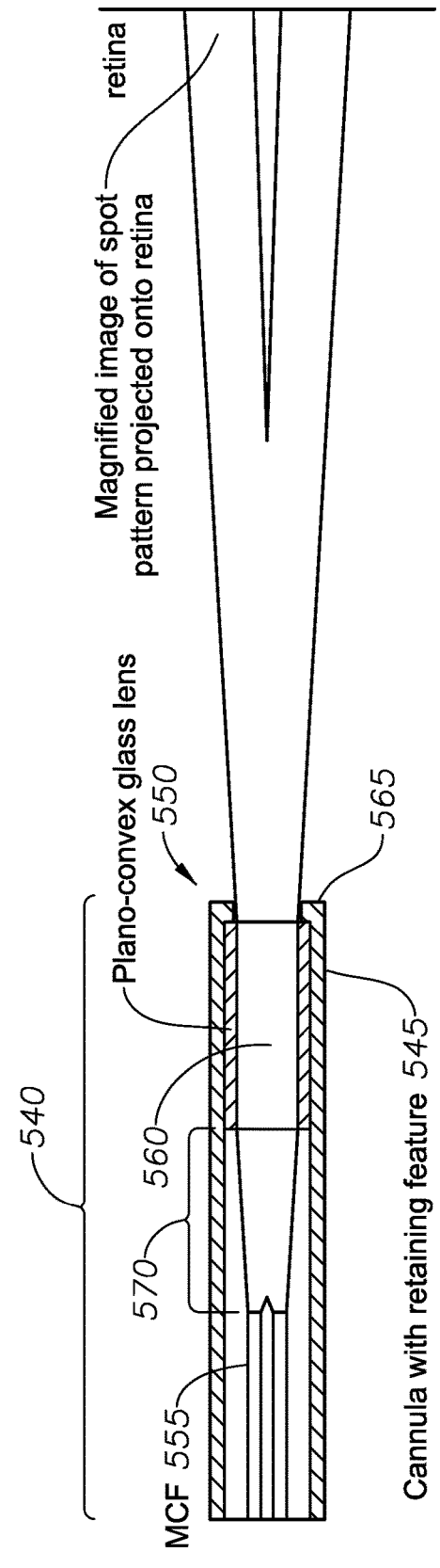
FIG. 5A
FIG. 5B

MULTIPLE-INPUT-COUPLED ILLUMINATED MULTI-SPOT LASER PROBE

PRIORITY CLAIM

This application claims the benefit of priority of U.S. Provisional Patent Application Ser. No. 62/630,865, filed on Feb. 15, 2018, U.S. Provisional Patent Application Ser. No. 62/597,550, filed on Dec. 12, 2017, U.S. Provisional Patent Application Ser. No. 62/598,653, filed on Dec. 14, 2017, and U.S. Provisional Patent Application Ser. No. 62/622,299, filed on Jan. 26, 2018, which are hereby incorporated by reference in their entirety as though fully and completely set forth herein.

BACKGROUND

Field of the Disclosure

The present disclosure relates to a multiple-input-coupled illuminated multi-spot laser system, and more specifically to systems and methods for creating multi-spot laser light beams, multiplexing an illumination light and the multi-spot laser light beams, and delivering the multiplexed light to a surgical handpiece via a multi-core optical fiber cable.

Description of Related Art

In many ophthalmic procedures a surgeon is required to use a variety of instruments in the patient's eye. For example, during a vitreoretinal surgery, a surgeon oftentimes manipulates a first handpiece for directing an illumination light beam onto the retinal surface in order to view patient anatomy and also manipulates an additional laser probe handpiece for delivering a laser treatment beam for treating the patient anatomy. However, there is a need for a multiple-input-coupled illuminated multi-spot laser system.

SUMMARY

The disclosed embodiments of the present technology relates to multiple-input-coupled illuminated multi-spot laser probes, systems for multiplexing an illumination light and multi-spot laser light, and methods for multiplexing an illumination light and multi-spot laser light for and delivering the multiplexed light onto patient anatomy.

Some embodiments of the disclosed technology involve a laser system with a therapeutic laser source, an aiming laser source, a diffractive optical element (DOE) that creates a multi-spot pattern of laser beams, an illumination system, and a multiplexing assembly that multiplexes the multi-spot pattern of laser beams with light from the illumination system. The disclosed technology also involves a condensing lens for focusing the multiplex light onto an interface with a multi-core optical fiber cable, selecting the materials used in a multi-core optical fiber cable, designing the condensing lens to ensure that the illumination beam and the laser aiming/treatment beams are propagated down an entire length of the multi-core optical fiber cable, and providing the ability of a surgical probe to simultaneously deliver illumination light and a multi-spot pattern of laser light beams to patient anatomy.

A laser system can include therapeutic laser source that produces a treatment laser beam having a wavelength substantially equal to 532 nm and directs the treatment laser beam to the DOE. The laser system can also include an aiming laser source that produces a laser aiming beam having a wavelength substantially equal to 635 nm and directs the laser aiming beam to a beamsplitter for directing the laser aiming beam to the DOE. The laser system can also include a shutter arranged between the therapeutic laser source and the DOE that alternatively blocks and transmits the treatment laser beam from reaching the DOE. The DOE creates a multi-spot laser pattern from the aiming laser beam and the treatment laser beam when the shutter transmits the treatment laser beam.

The laser system can also include an illumination system that emits substantially white light and a collimating lens that collimates the substantially white light received from the illumination system into an illumination beam. The laser system can also include a multiplexing beam splitter arranged to receive the illumination beam and the multi-spot laser pattern from the DOE, reflect the multi-spot laser pattern towards a condensing lens, and transmit the illumination beam from the collimating lens towards the condensing lens, thereby multiplexing the multi-spot laser pattern and the illumination beam. The condensing lens focuses a multiplexed beam of the illumination beam and the multi-spot pattern onto an interface with a port.

In some cases, the laser system includes beam compressor arranged between the therapeutic laser source and the DOE that collimates the treatment beam to a diameter selected based on the attributes of the DOE and a desired multi-spot pattern. Also, the laser system can include an optical element configured to transform a horizontally polarized treatment beam from the therapeutic laser source into a vertically polarized treatment beam. The optical element can be a half-wave plate, a quartz-crystal polarization rotator, or a metamaterial polarization rotator.

The laser system can also include a laser probe assembly having a multi-core optical fiber cable with a plurality of inner cores contained within an outer core. The plurality of inner cores contained within the outer core can match the multi-spot pattern created by the DOE.

In some cases, the multi-core optical fiber cable has a proximal end which, when coupled with the port, substantially abuts the interface in the port such that the focused, multiplexed multi-spot pattern and the illumination beam are focused on a proximal end of the multi-core optical fiber cable. The condensing lens and the materials for the multi-core optical fiber cable can be selected to ensure that the illumination beam and the laser aiming/treatment beams are propagated down an entire length of the multi-core optical fiber cable. Some cases involve the outer core surrounded by an outer-core cladding and a plurality of inner cores contained within the outer core, each inner core in the plurality of inner cores surrounded by an inner-core cladding. In these cases, a refractive index of the outer core is greater than a refractive index of the outer-core cladding, a refractive index of each of the inner cores in the plurality of inner cores is greater than a refractive index of the inner-core cladding, and a refractive index of each or the inner cores in the plurality of inner cores is larger than the refractive index of the outer-core cladding.

The laser probe assembly can also include a surgical handpiece at the distal end of the multi-core optical fiber cable. The surgical handpiece can have a probe tip with a lens that translates a geometry of the multiplexed multi-spot laser pattern and illumination beam from the distal end of the multi-core optical fiber cable onto a target surface.

Some embodiments of the present technology involve methods of multiplexing a multi-spot pattern of laser light beams with an illumination light beam. The methods can involve directing a laser light beams to an optical element for collimating the laser light beam and directing the collimated laser light beam to a diffractive optical element (DOE) to create a multi-spot laser pattern of laser light beams. Likewise, the methods can involve directing the multi-spot pattern of laser light beams and an illumination light beam to a beamsplitter. Next, methods can involve the beamsplitter reflecting the multi-spot pattern of laser light beams towards a condensing lens and transmitting the illumination light beam to the condensing lens, thereby multiplexing the multi-spot pattern of laser light beams and a transmitted illumination beam. The methods can also involve the condensing lens focusing the multiplexed multi-spot pattern of laser light beams and transmitted illumination beam onto an interface with a multi-core optical fiber cable. Also, the methods can involve directing the multiplexed multi-spot pattern of laser light beams and transmitted illumination beam through the multi-core optical fiber cable and onto a lens in a probe tip. The methods can also involve the lens translating the geometry of the multiplexed multi-spot laser pattern of laser light beams and illumination beam from the distal end of the multi-core optical fiber cable onto a target surface.

The disclosed technology can also involve creating an image of a multiplexed beam of multi-spot pattern of laser light beams and illumination light on patient anatomy by selecting materials for a multi-core optical fiber cable to ensure confinement of the beams within the various core regions as they propagate down the lengths fiber cable. The methods can involve determining a numerical aperture of laser light beams from a laser source and a numerical aperture of an illumination light beam from an illumination light source and selecting a condensing lens to focus the multiplexed multi-spot pattern of laser light beams and illumination beam onto an interface plane of the multi-core optical fiber cable to ensure confinement of the beams within the various core regions as they propagate down the lengths fiber cable.

The disclosed technology can also include a dual-portdual-port laser system with a first port for providing laser treatment beams and aiming laser beams to a laser probe and with an additional port for providing a multiplexed beam of illumination light and a multi-spot pattern of laser light beams to a multi-core optical fiber cable coupled with an illuminated multi-spot laser probe. The dual-port laser system can include a port selector for selectively directing the therapeutic laser beam to a first beam splitter and an additional beam splitter. The dual-port laser system can also include one or more aiming laser sources for directing an aiming laser beam to the first beam splitter and/or the second beam splitter. In some cases, the first beam splitter directs the treatment laser beam and the aiming laser beam to the first port and the additional beam splitter directs portions of the treatment laser beam and the aiming laser beam to a diffractive optical element (DOE). The DOE can create a multi-spot laser pattern from the treatment laser beam and the aiming laser beam.

In some cases, the dual-port laser system also includes a multiplexing beam splitter arranged to receive an illumination light beam from an illumination source and the multi-spot laser pattern from the DOE. The multiplexing beam splitter can reflect the multi-spot laser pattern towards a condensing lens and to transmit an illumination beam from a collimating lens towards the condensing lens, thereby multiplexing the multi-spot laser pattern and the illumination beam. Also, the condensing lens can focus a multiplexed beam of the illumination beam and the multi-spot pattern onto an interface in the additional port.

The dual-port laser system can include one or more beam detectors, power monitors, beam dumps, etc. Also the dual-port laser system can include an optical element for transforming a horizontally polarized treatment beam from the therapeutic laser source into a vertically polarized treatment beam. The optical element can be a half-wave plate, a quartz-crystal polarization rotator, or a metamaterial polarization rotator. The dual-port laser system can also include a shutter that selectively blocks and transmits the treatment laser beam from reaching the port selector.

BRIEF DESCRIPTION OF THE DRAWINGS

For a more complete understanding of the present technology, its features, and its advantages, reference is made to the following description, taken in conjunction with the accompanying drawings, in which:

FIG. 3G illustrates two light cones from the multi-spot pattern of laser light propagating down the lengths of a multi-core optical fiber cable in accordance with a particular embodiment of the present disclosure;

FIG. 3H illustrates the laser beams spread out to totally spatially fill the inner cores in accordance with a particular embodiment of the present disclosure;

FIG. 3I illustrates the distal end of the multi-core optical fiber cable with the laser beams spread out to totally spatially fill the inner cores in accordance with a particular embodiment of the present disclosure;

FIG. 3J illustrates a proximal, interface end of the multi-core optical fiber cable in accordance with a particular embodiment of the present disclosure with the illumination light spot lining up with the outer core;

FIG. 3K illustrates a light cone of the illumination light in accordance with a particular embodiment of the present disclosure with the light cone including a narrow half-angle portion of the light cone and a wide half-angle portion;

FIG. 3L illustrates the illumination beam spread out to totally spatially fill the outer core in accordance with a particular embodiment of the present disclosure;

FIG. 5A illustrates an open side view of a tip of a surgical hand probe in accordance with a particular embodiment of the present disclosure;

FIG. 5B illustrates an open side view of another tip of a surgical hand probe in accordance with a particular embodiment of the present disclosure;

DESCRIPTION

In a wide variety of medical procedures, laser light is used to assist the procedure and treat patient anatomy. For example, a vitreoretinal surgery oftentimes involves using a laser treatment beam for photocoagulation of retinal tissue. Vitreoretinal procedures commonly involve a laser probe that is capable of alternately emitting an aiming laser beam to select target spots on retinal tissue and emitting a treatment laser beam to perform the photocoagulation at the targeted spots. Frequently, the laser probe utilizes light in a red band of the electromagnetic spectrum for the aiming beam and light in a green band of the electromagnetic spectrum for the treatment beam. Also, during a panretinal laser photocoagulation procedure, a surgeon selects thousands of spots on retinal tissue to apply the treatment laser beam to, resulting in a very long and tedious procedure. Therefore, a laser probe capable of producing a multi-spot pattern of laser light is desirable.

Vitreoretinal procedures also benefit from illumination light being directed into the eye and onto retinal tissue. Vitreoretinal surgeons oftentimes use a laser probe handpiece for delivering the laser aiming beams and laser treatment beams and also use an additional handpiece for directing an illumination light beam onto the retinal surface in order to view patient anatomy.

The field of vitreoretinal surgery, as well as other medical laser procedures, would benefit from multiplexing an illumination light and multi-spot laser light. Accordingly, the technology described herein involves multiple-input-coupled illuminated multi-spot laser probes, adaptors and other systems for multiplexing an illumination light and multi-spot laser light, and methods for multiplexing an illumination light and multi-spot laser light and delivering the multiplexed light onto patient anatomy.

Figure 1A:
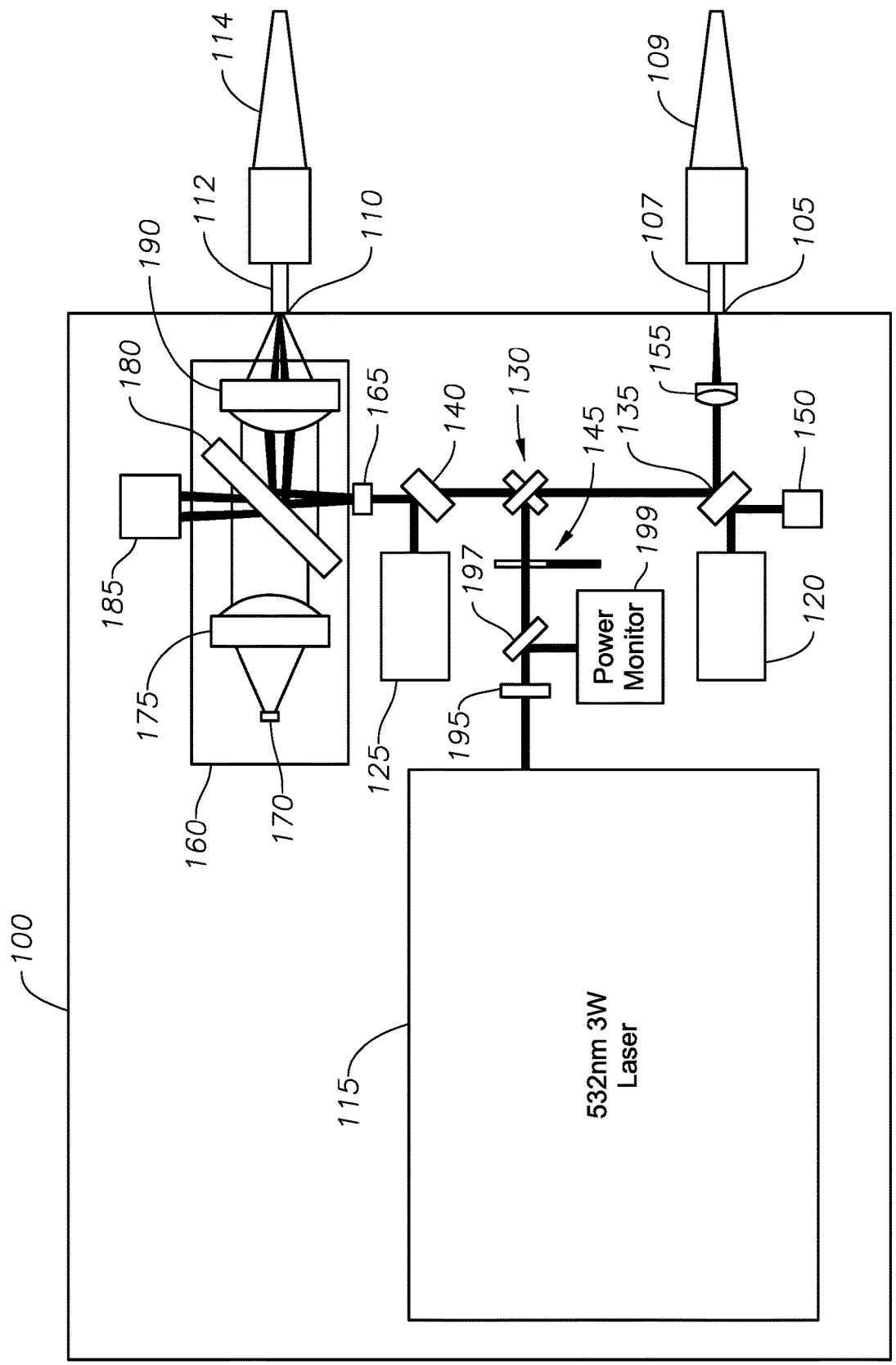
FIG. 1A illustrates a dual-port laser system in accordance with a particular embodiment of the present disclosure.

FIG. 1A illustrates a dual-port laser system 100 for providing aiming beams and treatment beams of laser light through a first port 105 and providing a multiplexed beam of illumination light and a multi-spot pattern of laser aiming beams and treatment beams through a second port 110 in accordance with a particular embodiment of the present disclosure.

The dual-port surgical laser system 100 includes a therapeutic laser source 115 for generating laser treatment beams used during an ophthalmic procedure. For example, the therapeutic laser source 115 can generate a surgical treatment beam with a wavelength of around 532 nanometers (nm). The dual-port surgical laser system 100 also includes two aiming laser sources 120, 125 which produce aiming laser beams.

The dual-port surgical laser system 100 also includes a port selector 130 that selectively directs the therapeutic laser beam to a first beam splitter 135 and the second beam splitter 140. Also, the two aiming laser sources 120, 125 respectively direct the aiming laser beams to the first beam splitter 135 and the second beam splitter 140.

The dual-port surgical laser system 100 also includes a shutter 145 arranged between the therapeutic laser source 115 and the port selector 130. The shutter 145 alternatively blocks and transmits the treatment laser beam from reaching the port selector 130. A surgeon or surgical staff member can control the shutter 145 (e.g. via a foot switch, voice commands, etc.) to emit the laser aiming beam and fire the treatment laser beam (i.e. open the shutter 145) to treat patient anatomy, e.g. photocoagulation. In each case, the first beam splitter 135 and the second beam splitter 140 direct the laser beams towards the first port 105 and the second port 110, respectively.

When the port selector 130 is in a first position, the first beam splitter 135 reflects portions of the treatment laser beam and transmits portions of the laser aiming beam towards the first port 105. The reflected portion of the laser aiming beam and the transmitted portion of the treatment laser beam can be directed towards a beam detector 150, a beam dump, a power monitor, etc. Also, a focusing lens 155 can be arranged between the first beam splitter 135 and the first port 105. The focusing lens 155 receives the treatment laser beam and the aiming laser beam from the first beam splitter 135 and focuses the treatment laser beam and the aiming laser beam onto an interface with an optical fiber 107 of a laser probe assembly 109 in the first port 105.

When the port selector 130 is in a second position, the second beam splitter 140 reflects a portion of the laser aiming beam from the aiming laser source 125 towards a diffractive optical element (DOE) 165. The second beam splitter 140 also transmits substantially all of the treatment laser beam through to the DOE 165. In some embodiments, the laser aiming beam and the treatment laser beam are collimated or substantially collimated when they fall incident on the DOE 165.

The DOE 165 receives the laser aiming beam and the treatment laser beam and creates a multi-spot laser pattern of laser light beams. The DOE 165 can be selected to diffract incident laser light into a multi-spot pattern that will align with an intended target geometry. For example, the DOE 165 can be selected to create a 2×2 array pattern of laser light beams that substantially matches a 2×2 array of inner cores of a multi-core optical fiber cable that delivers the multiplexed light to the surgical probe, as explained in greater detail below.

In some cases the DOE 165 is a moveable DOE 165 having a plurality of different diffraction regions selected for creating and transmitting various multi-spot patterns of laser light. For example, the DOE 165 can be a movable linear stage with three diffraction regions for creating and transmitting multi-spot patterns of one, two, or four beams to the multi-core optical fiber cable.

From the DOE 165, the multi-spot laser pattern of laser light beams travels towards a multiplexing assembly 160 before reaching the second port 110. The multiplexing assembly 160 of the dual-port surgical laser system 100 multiplexes the multi-spot pattern of laser light beams with an illumination light from an illumination light source 170. In some cases, the illumination light source 170 can include one or more of a xenon illuminator, an RGB light-emitting diode (LED) illuminator, a white light LED illuminator, a laser-pumped phosphor illuminator, a supercontinuum white laser illuminator, etc.

The multiplexing assembly 160 contains a collimating lens 175 for collimating or substantially collimating the illumination light from the illumination light source 170. Also, the multiplexing assembly 160 contains a beam splitter 180 that reflects a portion of the light spectrum and transmits a remaining portion of the light spectrum. More specifically, the beam splitter 180 can both: a) reflect the multi-spot pattern of laser aiming beams and treatment laser beams from the DOE 165 toward the second port 110 and b) transmit the illumination light (minus narrow bands of the spectrum corresponding with the laser aiming beam and the treatment laser beam) from the illumination light source 170 toward the second port 110. The beam splitter 180 reflects the narrow bands of the spectrum corresponding with the laser aiming beam and the treatment laser beam from the illumination light source 170 toward a beam detector 185, a beam dump, a power monitor, etc.

As explained above, vitreoretinal procedures frequently utilize light in a red band of the electromagnetic spectrum for a laser aiming beam and light in a green band of the electromagnetic spectrum for a laser treatment beam. Accordingly, the beam splitter 180 can be configured to highly reflect light in a narrow band of the red spectrum and a narrow band of the green spectrum and configured to transmit the remaining electromagnetic spectrum. In some embodiments, the beam splitter 180 reflects light in a first narrow band around 532 nanometers (nm) and in a second narrow band around 635 nm and transmits the remaining spectrum. The beam splitter 180 can be a dichroic beam splitter cube, a beamsplitter plate, etc.

The multiplexing assembly 160 also contains a condensing lens 190 arranged between the beam splitter 180 and the second port 110. The multiplexed light, including the Illumination light transmitted through the beam splitter 180 and the multi-spot pattern of laser light reflected by the beam splitter 180, falls incident on the condensing lens 190 before reaching the second port 110. Also, the condensing lens 190 is selected to precisely focus the multiplexed light onto an interface with a proximal end of a multi-core optical fiber cable 112 (as explained below) coupled with an illuminated multi-spot laser probe 114. As described below, selecting the materials used in a multi-core optical fiber cable and carefully focusing the multiplexed light using the condensing lens 190 can ensure that the illumination beam and the laser aiming/treatment beams are propagated down an entire length of the multi-core optical fiber cable, providing the ability of a surgical probe to simultaneously deliver illumination light and a multi-spot pattern of laser light beams to patient anatomy.

The dual-port surgical laser system 100 can also include an optical element 195 for transforming the polarization of the laser light emitted by the therapeutic laser source 115. It can be beneficial to have the linearly polarized treatment laser beam polarization and linearly polarized aiming laser beam polarization be oriented vertically because that will ensure the beamsplitter can be designed to most efficiently reflect the multi-spot pattern of laser beams while minimizing the transmitted white light discoloration and maximizing its throughput. In some cases, the aiming laser sources 120, 125 originate from cylindrical laser diodes that can be axially rotated to achieve vertical polarization. In some cases, the therapeutic laser source 115 can be a diode-pumped solid-state (DPSS) laser. In some cases, the therapeutic laser source 115 can be a semiconductor laser that naturally emits horizontally polarized light in a conventional mounting configuration. Therefore, to transform the horizontally polarized beam to a vertically polarized beam, the optical element 195 can rotate the polarization of the treatment laser beam. For example, optical element 195 can be a half-wave plate, a quartz-crystal polarization rotator, or a metamaterial polarization rotator.

In some cases, the dual-port surgical laser system 100 can also include a mirror 197 for directing a small portion of the treatment laser beam from the therapeutic laser source 115 to a power monitor 199.

Figure 1B:
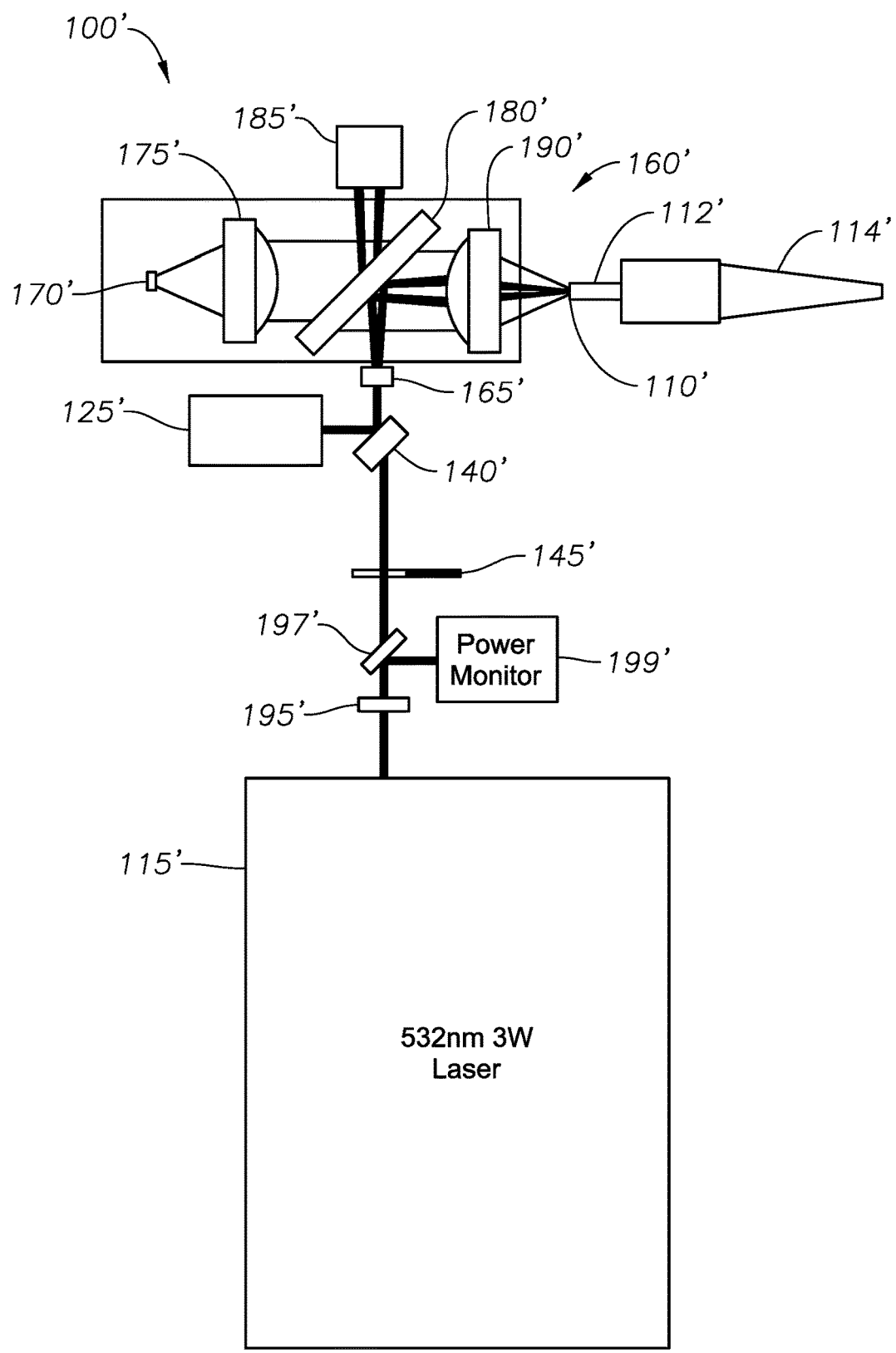
FIG. 1B illustrates a surgical laser system for providing a multiplexed beam of illumination light and a multi-spot pattern of laser aiming beams and treatment beams in accordance with a particular embodiment of the present disclosure.

FIG. 1B illustrates another surgical laser system 100' for providing a multiplexed beam of illumination light and a multi-spot pattern of laser aiming beams and treatment beams in accordance with a particular embodiment of the present disclosure. The surgical laser system 100' includes a therapeutic laser source 115' for generating laser treatment beams used during an ophthalmic procedure and an aiming laser source 125' that produces an aiming laser beam. The therapeutic laser source 115' and the aiming laser source 125' can both direct their emitted beams to a beam splitter 140' that reflects the laser aiming beam and transmits the laser treatment beam towards a diffractive optical element (DOE) 165'.

The DOE 165' receives the laser aiming beam and the treatment laser beam and creates a multi-spot laser pattern of laser light beams. For example, a DOE 165' can be selected to create a 2×2 array pattern of laser light beams that substantially matches a 2×2 array of inner cores of a multi-core optical fiber cable that delivers the multiplexed light to the surgical probe, as explained in greater detail below. From the DOE 165', the multi-spot laser pattern of laser light beams travels towards a multiplexing assembly 160' before reaching a port 110'.

The multiplexing assembly 160' of the surgical laser system 100' multiplexes the multi-spot pattern of laser light beams with an illumination light from an illumination light source 170'. The multiplexing assembly 160' contains a collimating lens 175' for collimating or substantially collimating the illumination light from the illumination light source 170. Also, the multiplexing assembly 160' contains a beam splitter 180' that both: a) reflects the multi-spot pattern of laser aiming beams and treatment laser beams from the DOE 165' toward the port 110' and b) transmits the illumination light (minus narrow bands of the spectrum corresponding with the laser aiming beam and the treatment laser beam) from the illumination light source 170' toward the port 110'. The beam splitter 180' reflects the narrow bands of the spectrum corresponding with the laser aiming beam and the treatment laser beam from the illumination light source 170' toward a beam detector 185', a beam dump, a power monitor, etc.

The multiplexing assembly 160' further contains a condensing lens 190' arranged between the beam splitter 180' and the port 110'. The condensing lens 190' can be selected to precisely focus the multiplexed light onto an interface with a proximal end of a multi-core optical fiber cable 112' (as explained below) coupled with an illuminated multi-spot laser probe 114'.

The surgical laser system 100' can also include one or more of a shutter 145' arranged between the therapeutic laser source 115' and the DOE 165', an optical element 195' for transforming the polarization of the laser light emitted by the therapeutic laser source 115', and a mirror 197' for directing a portion of the treatment laser beam from the therapeutic laser source 115' to a power monitor 199'.

Figure 2:
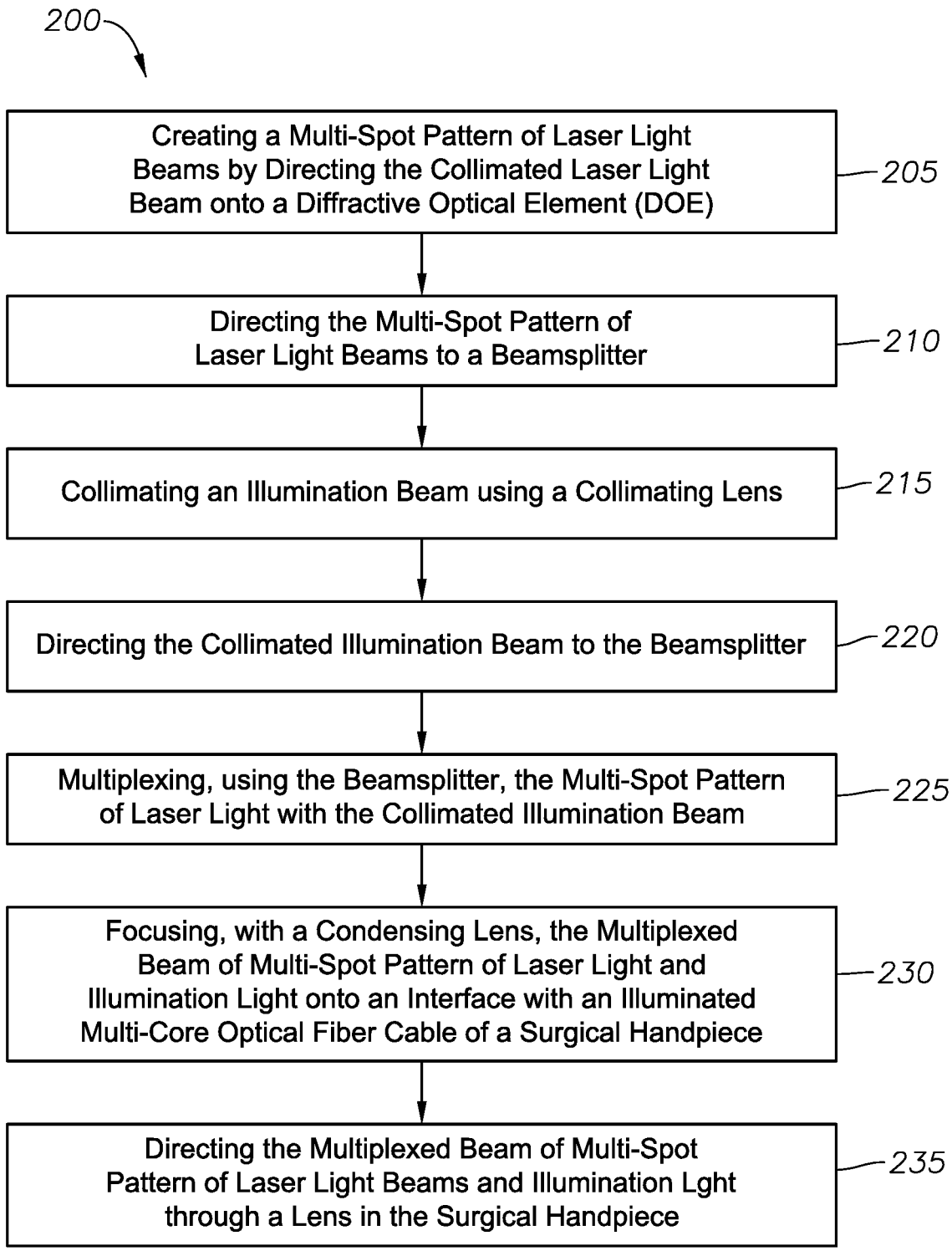
FIG. 2 illustrates a method for multiplexing a multi-spot pattern of laser light beams and illumination light in accordance with a particular embodiment of the present disclosure.

FIG. 2 illustrates a method 200 for multiplexing a multi-spot pattern of laser light beams and illumination light in accordance with a particular embodiment of the present disclosure. The method 200 involves creating a multi-spot pattern of laser light beams by directing the collimated laser light beam onto a diffractive optical element (DOE) at step 205, and directing the multi-spot pattern of laser light beams to a beamsplitter at step 210.

The method 200 also involves collimating an illumination beam using a collimating lens at step 215 and directing the collimated illumination beam to a beamsplitter at step 220. Next, the method 200 involves multiplexing, using the beamsplitter, the multi-spot pattern of laser light with the collimated illumination beam at step 225. More specifically, in some cases, multiplexing the multi-spot pattern of laser light with the collimated illumination beam can involve the beamsplitter reflecting laser aiming and treatment beams from the surgical laser system toward a condensing lens and transmitting the illumination light from the illumination light source towards the condensing lens.

The method 200 also involves focusing, with a condensing lens, the multiplexed beam of multi-spot pattern of laser light and illumination light onto an interface with a multi-core optical fiber cable of a surgical handpiece at step 230 and, subsequently, directing the multiplexed beam of multi-spot pattern of laser light beams and illumination light through a lens in the surgical handpiece at step 235, as described in more detail below.

In some cases, the intensities of the white illumination and the laser aiming beams can be adjusted (e.g. at the illumination light source and surgical laser system, respectively) to provide the right amount of laser aiming beam contrast against the white while providing enough white illumination to easily see the retina.

As mentioned above, a condensing lens can be selected to precisely focus the multiplexed light onto an interface of the terminal end of the multi-core optical fiber cable such that an illumination beam and laser aiming/treatment beams are propagated down an entire length of the multi-core optical fiber cable and into a surgical hand probe. More specifically, the condensing lens can be selected such that resulting light cones of light from the illumination beam and laser aiming/treatment beams have an acceptance angle and a numerical aperture (NA) to interface with the various fiber core and cladding materials used in the multi-core optical fiber cable such that the illumination beam and the laser aiming/treatment beams are propagated down the appropriate core fibers the entire length of the multi-core optical fiber cable.

Figure 3A:
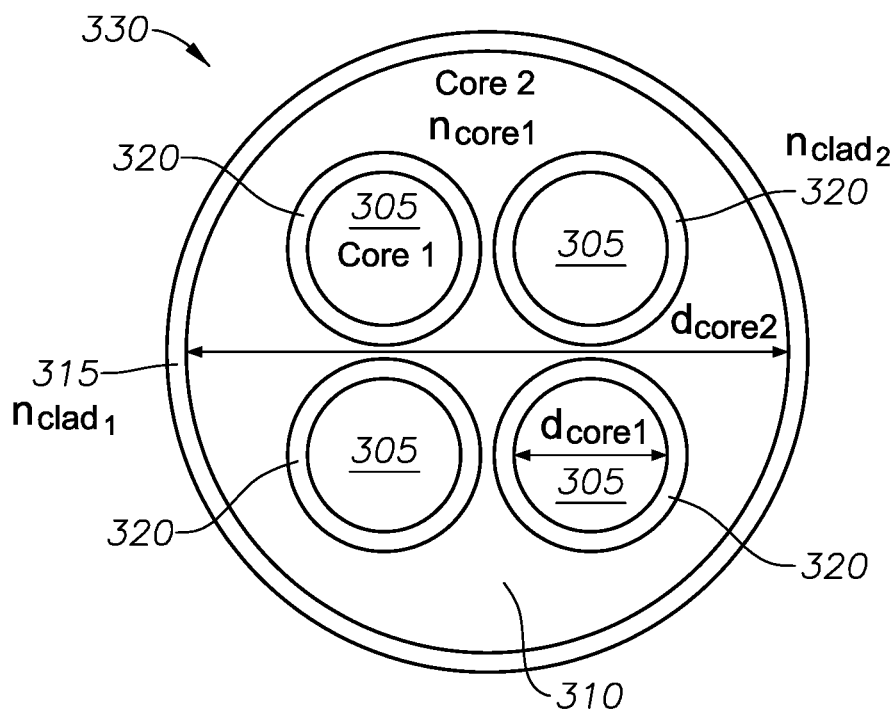
FIG. 3A illustrates the top view of a proximal end of a multi-core optical fiber cable in accordance with a particular embodiment of the present disclosure.

FIG. 3A illustrates the top view of a proximal end of a multi-core optical fiber cable 330 according to some embodiments of the present disclosure. The multi-core fiber cable 330 can include four inner core fibers 305 with a relatively small-diameter and a relatively small NA inside of an outer core fiber 310 having a relatively large diameter and a relatively large NA. The outer core fiber 310 can be contained within an outer-core cladding 315 with refractive index ($n_{clad1}$) and the inner core fibers 305 can be contained within an inner-core cladding 320 with refractive index ($n_{clad2}$). Also, the outer core 310 has a core diameter ($d_{core2}$) and the inner cores 305 can have a core diameter ($d_{core1}$).

Figure 3B:
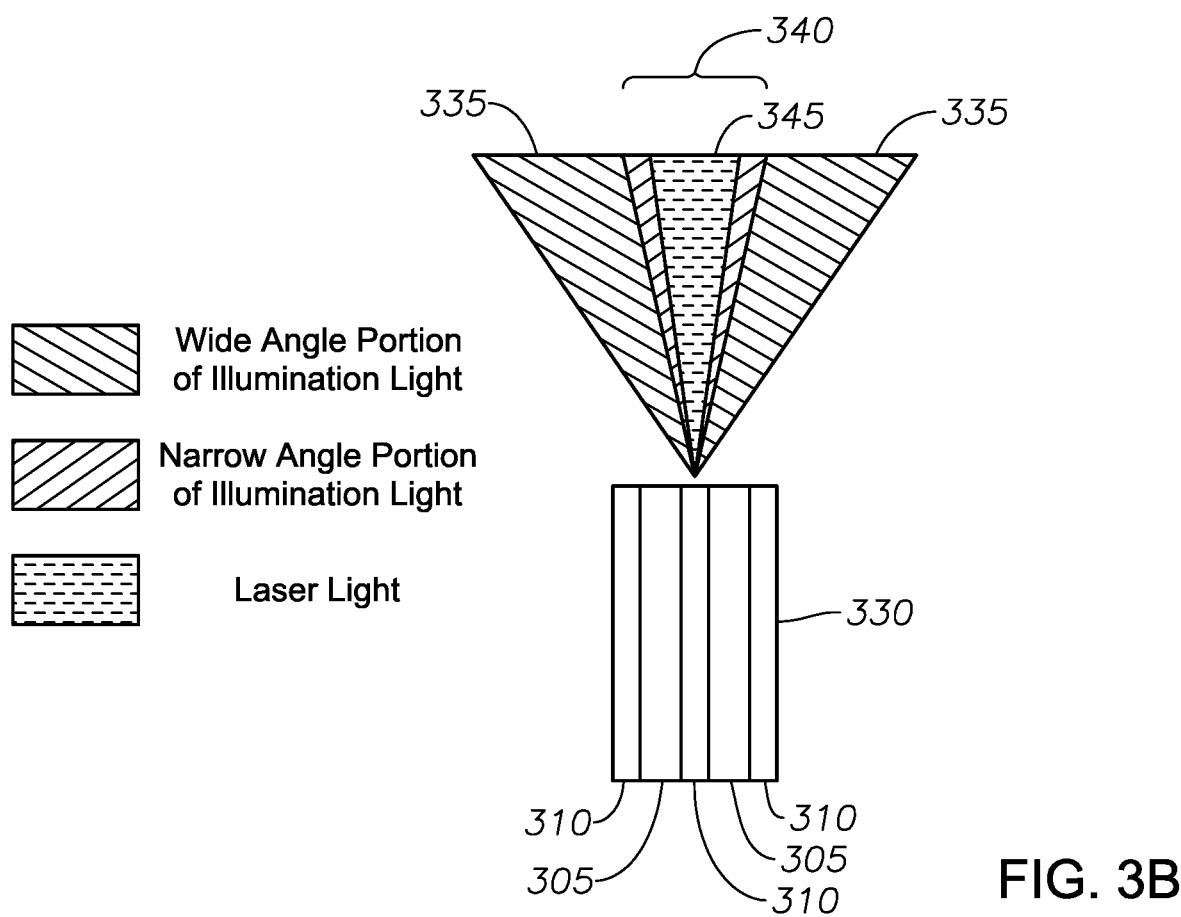
FIG. 3B illustrates a side view of the interface of a plurality of light cones onto a terminal end of a multi-core optical fiber cable in accordance with a particular embodiment of the present disclosure.

FIG. 3B illustrates a side view of the interface of a plurality of light cones 335, 340, 345 onto a terminal end of a multi-core optical fiber cable 330 according to some embodiments of the present disclosure. The multi-core optical fiber cable 330 in FIG. 3B shows the outer core fiber 310 and two of the inner core fibers 305. For the sake of image clarity, the outer-core cladding 315 and the inner-core cladding 320 is not depicted in FIG. 3B. Also represented are a wide-angle portion of the illumination light cone 335, a narrow angle portion of the illumination light cone 340, and the laser light cone 345. The selection of the condensing lens is related to the half-angle of each of the light cones. Therefore, selecting a condensing lens can involve selecting a condensing lens based on the NA of the light, the acceptance angle of the light cones, and the refractive indices of the materials of the outer core fiber 310, the outer-core cladding 315, the inner core fibers 305, and the inner-core cladding 320.

The condensing lens is designed to focus laser light down onto the multi-core fiber interface with the desired beam NA. The refractive indices of the inner core fibers 305 and inner cladding-core claddings 320 are selected according to an NA calculation (shown below) so that the NA of the inner cores is equal to or greater than the beam NA, thereby ensuring confinement of the beams within the inner core regions as they propagate down the lengths of the inner core fibers 305.

Referring again to FIG. 3A, a refractive index ($n_{core2}$) of the outer core fiber 310 is greater than a refractive index ($n_{clad2}$) of the outer-core cladding 315. Also, a refractive index ($n_{core1}$) of each of the inner cores fibers 305 is greater than a refractive index ($n_{clad1}$) of the inner-core cladding 320. Further, the refractive index (morel) of each or the inner cores fibers 305 is larger than the refractive index ($n_{clad1}$) of the outer-core cladding 315.

The numerical aperture ($NA_2$) for the outer core fiber 310 and the outer-core cladding 315 can be calculated as:

$$NA_2 = \sqrt{(n_{core2})^2 - (n_{clad2})^2}$$

Likewise, the numerical aperture ($NA_1$) for the inner core fibers 305 and the inner-core cladding 320 can be calculated as:

$$NA_1 = \sqrt{(n_{core1})^2 - (n_{clad1})^2}$$

In some embodiments of the present technology, the materials for the outer core fiber 310, the outer-core cladding 315, the inner core fibers 305, and the inner-core cladding 320 are selected such that $NA_2$ is much larger than $NA_1$. In a specific embodiment, the outer core can be an undoped fused silica with an index of substantially 1.46.

Also, in some embodiments, the red aiming laser beam has an NA of about 0.044 and the green treatment laser beam has an NA of about 0.0657. Therefore, as long as the numerical aperture ($NA_1$) for the inner core fiber 305 is larger than 0.0657, the red and green laser beams will remain confined within the inner cores 305 as they propagate down the probe. So, a silica fiber with an NA of 0.22 used for the outer core 310 may confine the laser beams.

Also, the illumination light can have an NA of around 0.63 and the core diameter can be configured to under-fill or match $d_{core2}$. The numerical aperture ($NA_2$) for the outer core fiber 310 and the outer-core cladding 315 can be designed to have a fiber NA≥0.63, e.g. a borosilicate fiber construction.

When the illumination beam etendue is greater than outer core 310 etendue, then coupling efficiency into outer core 310 is less than one hundred percent regardless of condenser lens focal length choice. However, if the illumination beam etendue (which is the product of the illumination beam angular width and spot width) is less than the outer core 310 etendue, then one hundred percent coupling efficiency (neglecting Fresnel reflection losses) can occur if the condensing lens focus is designed correctly. If the condensing lens has too short of a focus, the converging beam may have an NA greater than core 310 NA, and coupling efficiency may be degraded. If the condensing lens has too long of a focal length, then the focused beam diameter may be larger than the 310 diameter, and coupling efficiency may be degraded. However if the condensing lens focal length is adjusted so that beam NA is less than or equal to the fiber NA, and the beam diameter is less than or equal to the fiber core diameter, then one hundred percent or near one hundred percent coupling efficiency can occur.

Therefore, the illumination beam may both spatially and angularly underfill the outer core 310, which will permit spatial and angular misalignments without a loss of coupling efficiency. Also, since the illumination beam NA is >>NA1, off-axis rays can frequently pass in and out of the inner cores 305 and inner core cladding 320 as the rays propagate down the length of the multi-core optical fiber cable 330.

Figure 3C:
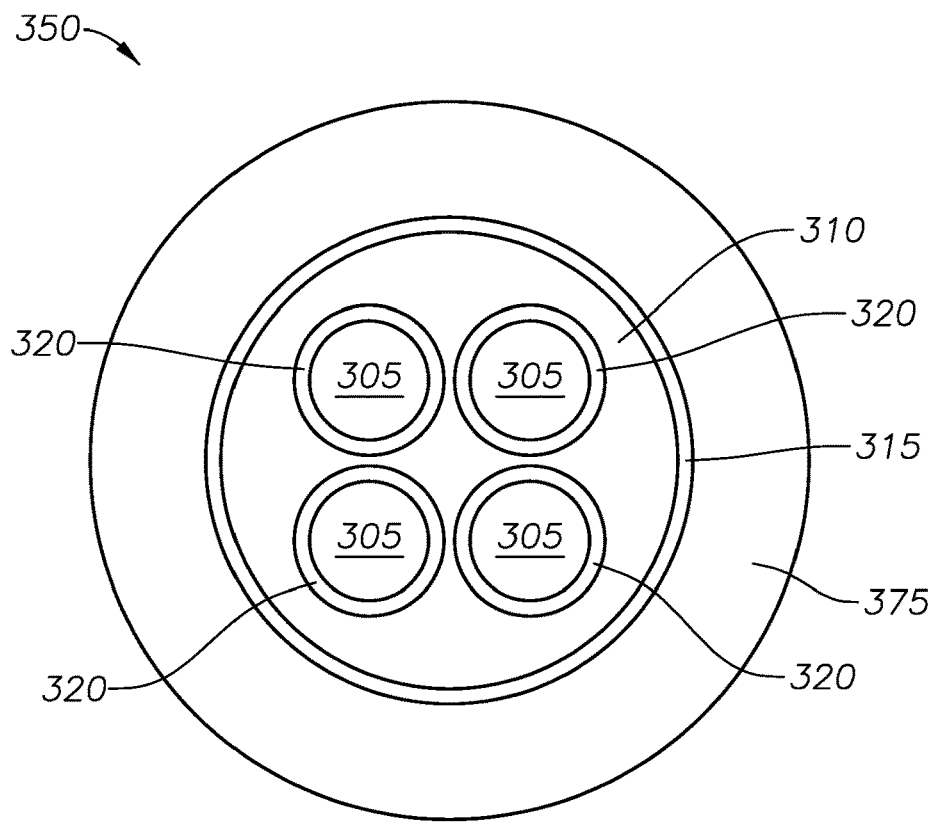
FIG. 3C illustrates the cut-away view of a multi-core optical fiber cable in accordance with a particular embodiment of the present disclosure.

FIG. 3C illustrates the cut-away view of a multi-core optical fiber cable 350 according to some embodiments of the present disclosure. The multi-core fiber cable 350 includes four fused silica inner core fibers 305 with a 75 micrometer diameter and a numerical aperture (NA) of 0.22 inside of a non-doped fused silica outer core fiber 310 having a 300 micrometer diameter and an NA of 0.47. The outer core fiber 310 can be contained within low-index polymer cladding 315 having a 25 micrometer thickness and the inner core fibers 305 can be contained within fluorine-doped fused silica inner-core cladding 320 having a 15 micrometer thickness. The multi-core optical fiber cable 350 can be further contained in an Ethylene Tetrafluoroethylene (ETFE) coating 375.

The four fused silica inner core fibers 305 have a refractive index of 1.46 at 532 nanometers. The non-doped fused silica outer core fiber 310 have a refractive index of 1.46 at 532 nanometers. The fluorine-doped fused silica inner-core cladding 320 can have a refractive index of 1.4433 at 532 nanometers. The low-index polymer cladding 315 can have a refractive index of 1.38228 at 532 nanometers.

Figure 3D:
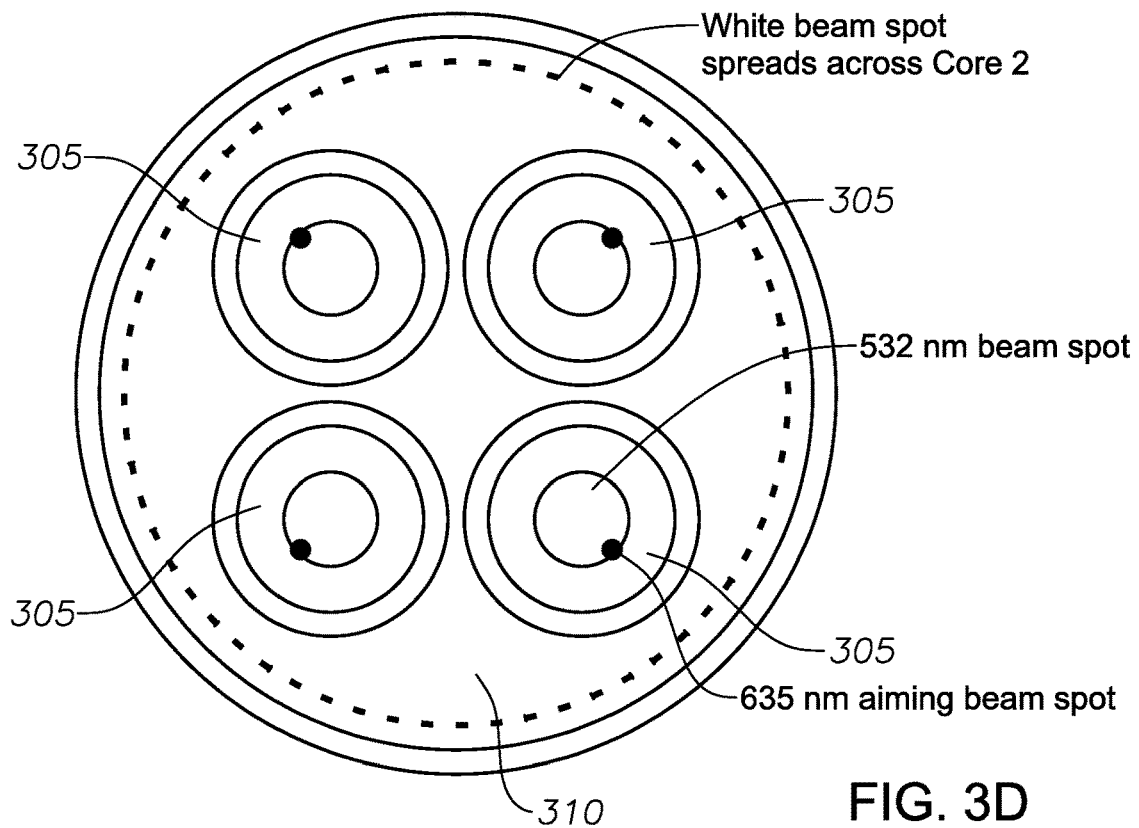
FIG. 3D illustrates a proximal, interface end of the multi-core optical fiber cable in accordance with a particular embodiment of the present disclosure with a red laser aiming beam spot and a green laser treatment beam spot lining up with the inner cores and the illumination light beam spot lining up with the outer core.
Figure 3E:
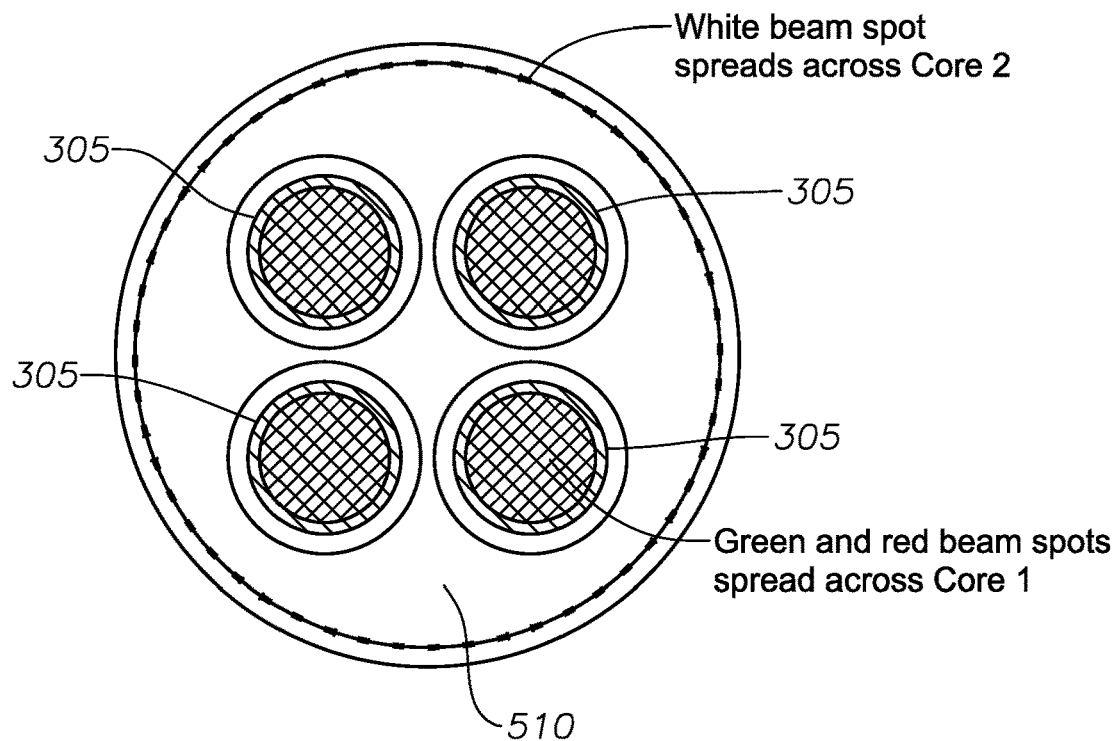
FIG. 3E illustrates the distal end of the multi-core optical fiber cable in accordance with a particular embodiment of the present disclosure with all three beams spread out to totally spatially fill their respective cores.

FIG. 3D illustrates a proximal, interface end of the multi-core optical fiber cable with a red laser aiming beam spot and a green laser treatment beam spot lining up with the inner cores 305 and the illumination light beam spot lining up with the outer core 310. FIG. 3E illustrates the distal end of the multi-core optical fiber cable with all three beams spread out to totally spatially fill their respective cores. FIGS. 3F-3L illustrate the propagation of the multiplexed light through the multi-core optical fiber cable.

Figure 3F:
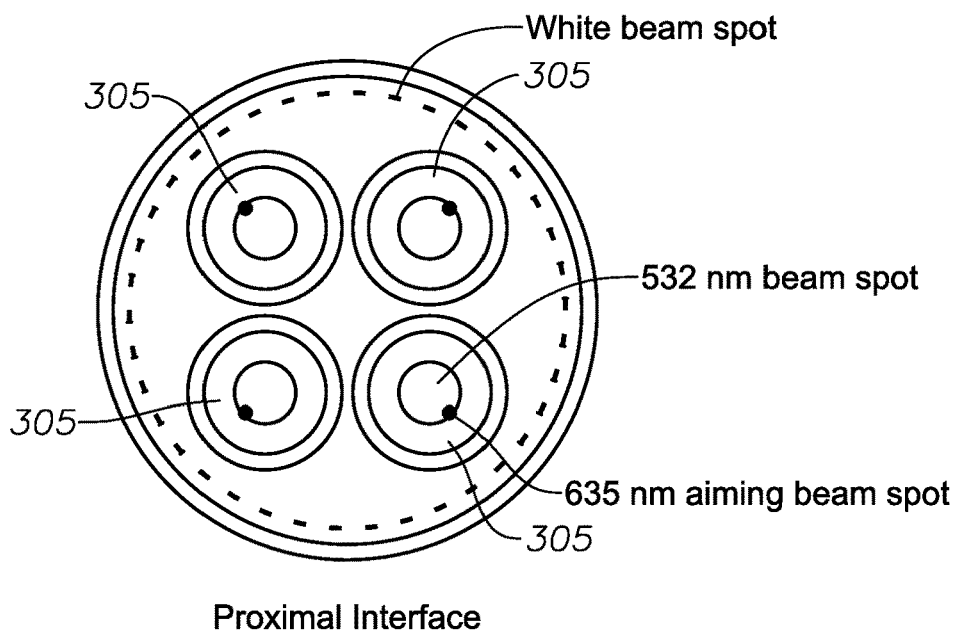
FIG. 3F illustrates a proximal, interface end of the multi-core optical fiber cable in accordance with a particular embodiment of the present disclosure with a red laser aiming beam spot and a green laser treatment beam spot lining up with the inner cores.

FIG. 3F illustrates a proximal, interface end of the multi-core optical fiber cable with a red laser aiming beam spot and a green laser treatment beam spot lining up with the inner cores 305. FIG. 3G illustrates two light cones from the multi-spot pattern of laser light (with the multiplexed illumination light emitted for image clarity) propagating down the lengths of a multi-core optical fiber cable. FIG. 3H illustrates the laser beams spread out to totally spatially fill the inner cores 305. Similarly, FIG. 3I illustrates the distal end of the multi-core optical fiber cable with the laser beams spread out to totally spatially fill the inner cores 305.

FIG. 3J illustrates a proximal, interface end of the multi-core optical fiber cable with the illumination light spot lining up with the outer core 310. FIG. 3K illustrates a light cone of the illumination light (with the multiplexed multi-spot pattern of laser light beams emitted for image clarity), with the light cone including a narrow half-angle portion of the light cone and a wide half-angle portion. The narrow half-angle portion of the light cone propagates the lengths of the outer cores 310, but is excluded from the inner cores 305. The wide half-angle portion of the illumination light cone fills the length of the outer core 310 and the inner cores 305.

Figure 3M:
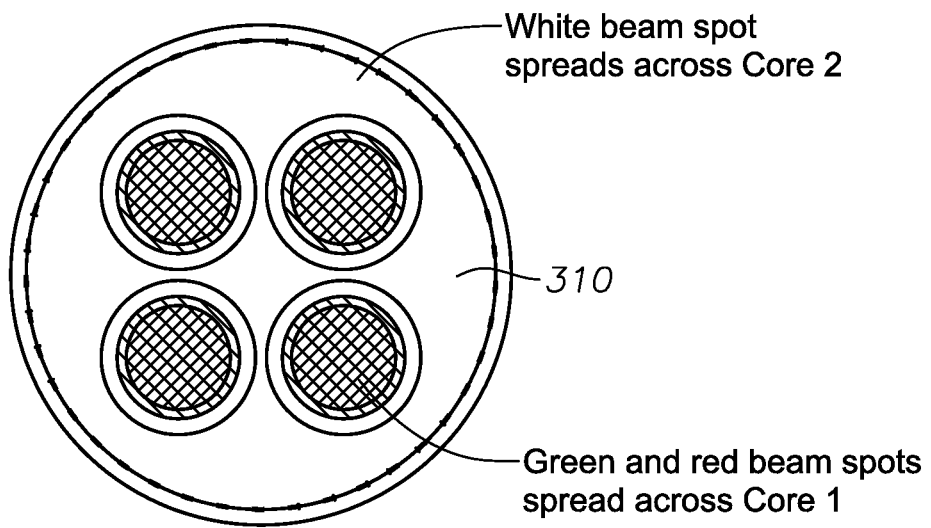
FIG. 3M illustrates the distal end of the multi-core optical fiber cable in accordance with a particular embodiment of the present disclosure with the illumination beam spread across the outer cores and the inner cores.

FIG. 3L illustrates the illumination beam spread out to totally spatially fill the outer core 310. Similarly, FIG. 3M illustrates the distal end of the multi-core optical fiber cable with the illumination beam spread across the outer cores 310 and the inner cores 305.

Figure 3N:
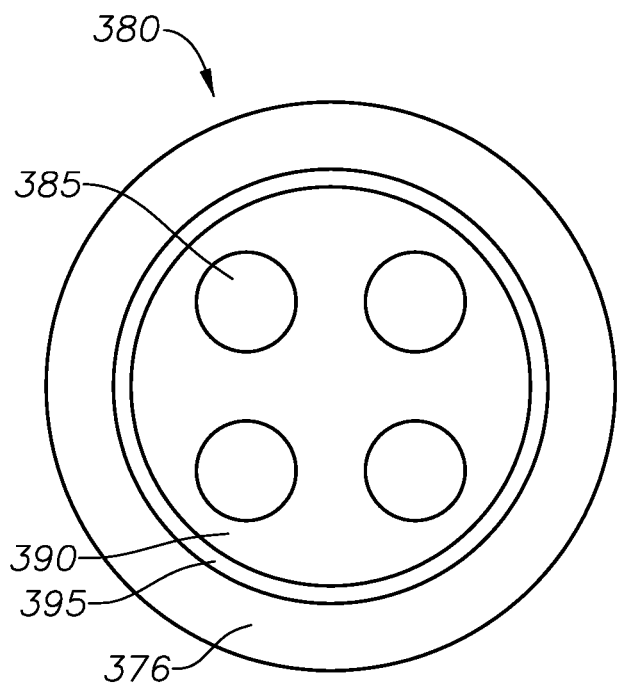
FIG. 3N illustrates the cut-away view of another multi-core optical fiber cable in accordance with a particular embodiment of the present disclosure.

FIG. 3N illustrates the cut-away view of another multi-core optical fiber cable 380 according to some embodiments of the present disclosure. The multi-core fiber cable 380 includes four germanium-doped silica inner core fibers 385 with a 75 micrometer diameter and a numerical aperture (NA) of 0.22 inside of a non-doped fused silica outer core fiber 390 having a 300 micrometer diameter and an NA of 0.47. The outer core fiber 390 can be contained within low-index polymer cladding 395 having a 25 micrometer thickness. The multi-core optical fiber cable 380 can be further contained in an Ethylene Tetrafluoroethylene (ETFE) coating 376.

The four germanium-doped silica inner core fibers 385 have a refractive index of substantially 1.47648 at 532 nanometers. The non-doped fused silica outer core fiber 390 have a refractive index of 1.46 at 532 nanometers. The low-index polymer cladding 395 can have a refractive index of 1.38228 at 532 nanometers.

While specific geometries of the multi-core optical fiber cable are shown explicitly herein, those with ordinary skill in the art having the benefit of the present disclosure will readily appreciate that a wide variety of configurations for the multi-core optical fiber cable are possible. In the configuration shown in FIGS. 3A-3N, the white illumination spot at the distal end of the multi-core optical fiber is somewhat larger than the 2×2 array of laser spots. In some cases, this geometry is desired, because it provides illumination into both the retinal treatment target area as well as some surrounding retina and because the illumination spot small enough to keep the white light fairly concentrated. Also, the geometry enables adequate white irradiance at the retina with a relatively small core diameter fiber. Furthermore, as explained above, the intensities of the white illumination and the laser aiming beams can be adjusted (e.g., at the Illumination Light Source and Surgical Laser System, respectively) to provide the right amount of laser aiming beam contrast against the white while providing enough white illumination to easily see the retina.

Figure 4:
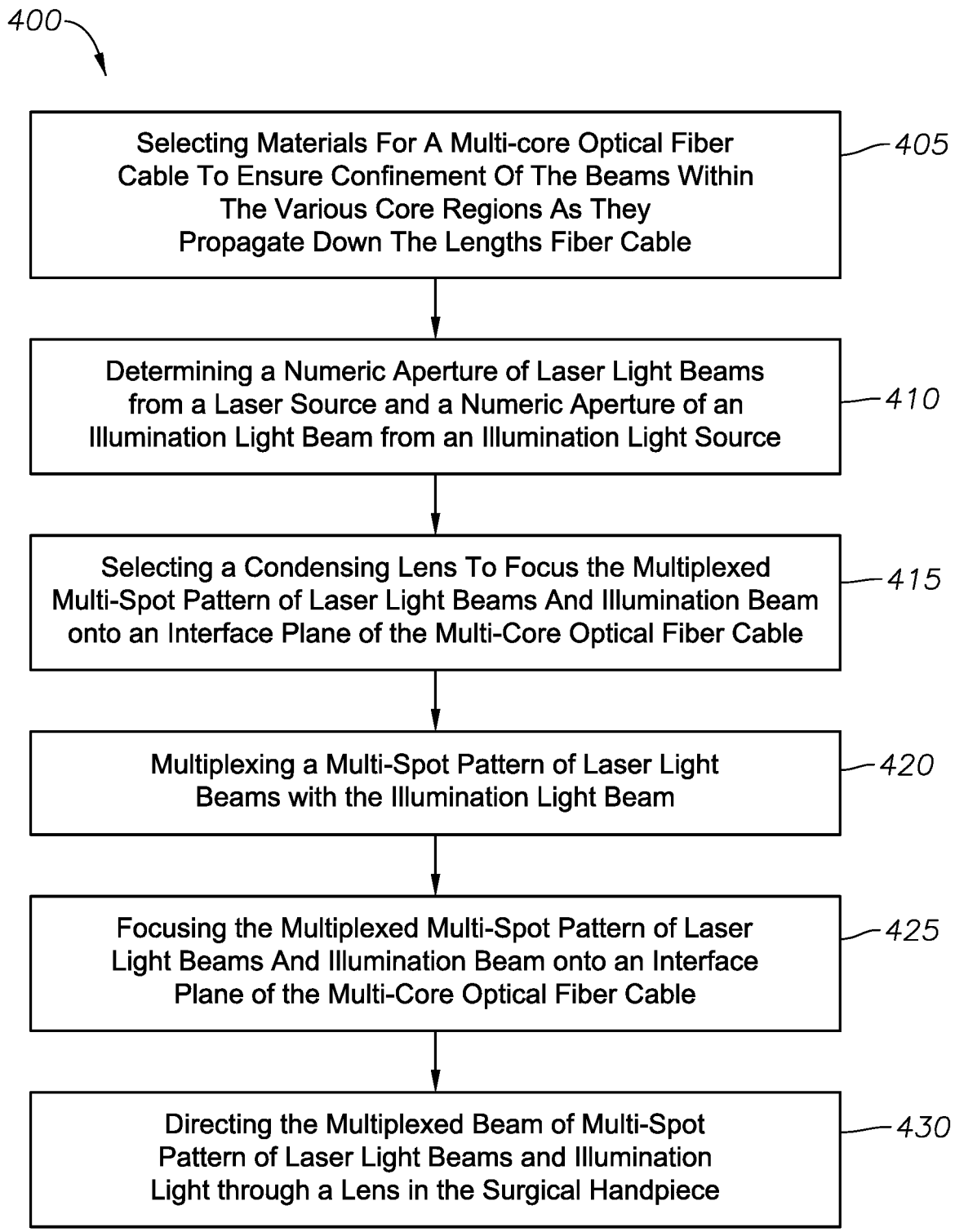
FIG. 4 illustrates a method of creating an image of a multiplexed beam of multi-spot pattern of laser light beams and illumination light in accordance with a particular embodiment of the present disclosure.

FIG. 4 illustrates a method 400 of creating an image of a multiplexed beam of multi-spot pattern of laser light beams and illumination light. The method involves selecting materials for a multi-core optical fiber cable to ensure confinement of the beams within the various core regions as they propagate down the lengths fiber cable, as explained above, at step 405. The method 400 also involves determining a numerical aperture of laser light beams from a laser source and a numerical aperture of an illumination light beam from an illumination light source at step 410 and selecting a condensing lens to focus the multiplexed multi-spot pattern of laser light beams and illumination beam onto an interface plane of the multi-core optical fiber cable at step 415.

Next, the method 400 involves multiplexing a multi-spot pattern of laser light beams with the illumination light beam at step 420, focusing the multiplexed multi-spot pattern of laser light beams and illumination beam onto an interface plane of the multi-core optical fiber cable at step 425, and directing the multiplexed beam of multi-spot pattern of laser light beams and illumination light through a lens in the surgical handpiece at step 430.

As explained above, a wide variety of configurations for the multi-core optical fiber cable are possible. For example, an incoherent white light illumination light source can be replaced with a white laser system (e.g. a supercontinuum laser system). In this case, the etendue of the white laser beam may be small enough that it is less than the nanofiber etendue and can be efficiently coupled into the nanofiber, such that a multi-core optical fiber cable as described above can be used to deliver multiplexed laser aiming and treatment beams and white laser illumination.

In some embodiments of the present disclosure, the distal end of the multi-core optical fiber cable terminates within a tip of a surgical hand probe that is inserted into a patient's eye. The tip of the surgical hand probe can also include a lens to image the multiplexed beams onto patient anatomy, e.g. the retina.

FIG. 5A illustrates an open side view of a tip 505 of a surgical hand probe according to some embodiments of the present disclosure. The probe tip 505 can comprise a cannula 535 (e.g., a stainless steel cannula) with a cannula distal end 530 and the probe tip containing the multi-core optical fiber 510 and a lens 515. The lens 515 can be a graded-index (GRIN) lens and an air gap 525 can be left open between the GRIN lens 515 and the distal end of the multi-core optical fiber 510. The air gap 525 can be sized such that the light emitted from the multi-core optical fiber 510 experiences an amount of spread before falling incident on the GRIN lens 515 and such that the GRIN lens 515 images the light onto the patient anatomy.

In some cases, no air gap is allowed between the distal end of the multi-core optical fiber 510 and the proximal end of the lens 515. Here, the multi-core optical fiber 510 and lens 515 are substantially butted up against one other with positive pressure to avoid air-gap tolerance concerns, allowing less chance for peripheral off-axis rays to travel far enough off axis to reflect off of the cylindrical side wall of the GRIN lens. However, using a conventional lens instead of the GRIN lens involves an air gap between the multi-core optical fiber 510 and lens 515 to focus the light properly.

In some cases, the lens 515 is secured within the probe tip 505 with an optical adhesive 520. As shown in FIG. 5A, a multi-spot pattern of green, 532 nm laser light is projected retinal tissue located 4 millimeters from the cannula distal end 530.

FIG. 5B illustrates an open side view of another tip 540 of a surgical hand probe according to some embodiments of the present disclosure. Again, the probe tip 540 can comprise a cannula 545 with a cannula distal end 550 and the probe tip containing the multi-core optical fiber 555 and a lens 560. The lens 560 illustrated in FIG. 5B is a Plano-convex glass lens. Also, the Plano-convex lens 560 is secured in the cannula 545 by a retaining feature 565. Again, an air gap 570 can be sized such that the light emitted from the multi-core optical fiber 555 experiences an amount of spread before falling incident on the Plano-convex lens 560 and such that the Plano-convex lens 560 images the light onto the patient anatomy.

As explained above, a surgical laser system (e.g., surgical laser systems 100, 100') can alternatively generate a surgical treatment beam with a wavelength of around 532 nanometers (nm) (i.e., green) and a laser aiming beam with a wavelength of around 635 nm (i.e., red). However, red and green incident laser light diffract off a DOE with different diffraction angles. When the laser beams are not collimated then their focus is also affected, i.e. red and green will focus at different axial locations. This greatly complicates trying to focus both green and red laser beams into the same inner-core regions of the multi-core fiber, as explained above. Also, the DOE can have a fixed requirement for the collimated laser beam diameter. Therefore some embodiments of the disclosed technology involve collimating the multiple beams with a selected beam diameter for the DOE.

Figure 6:
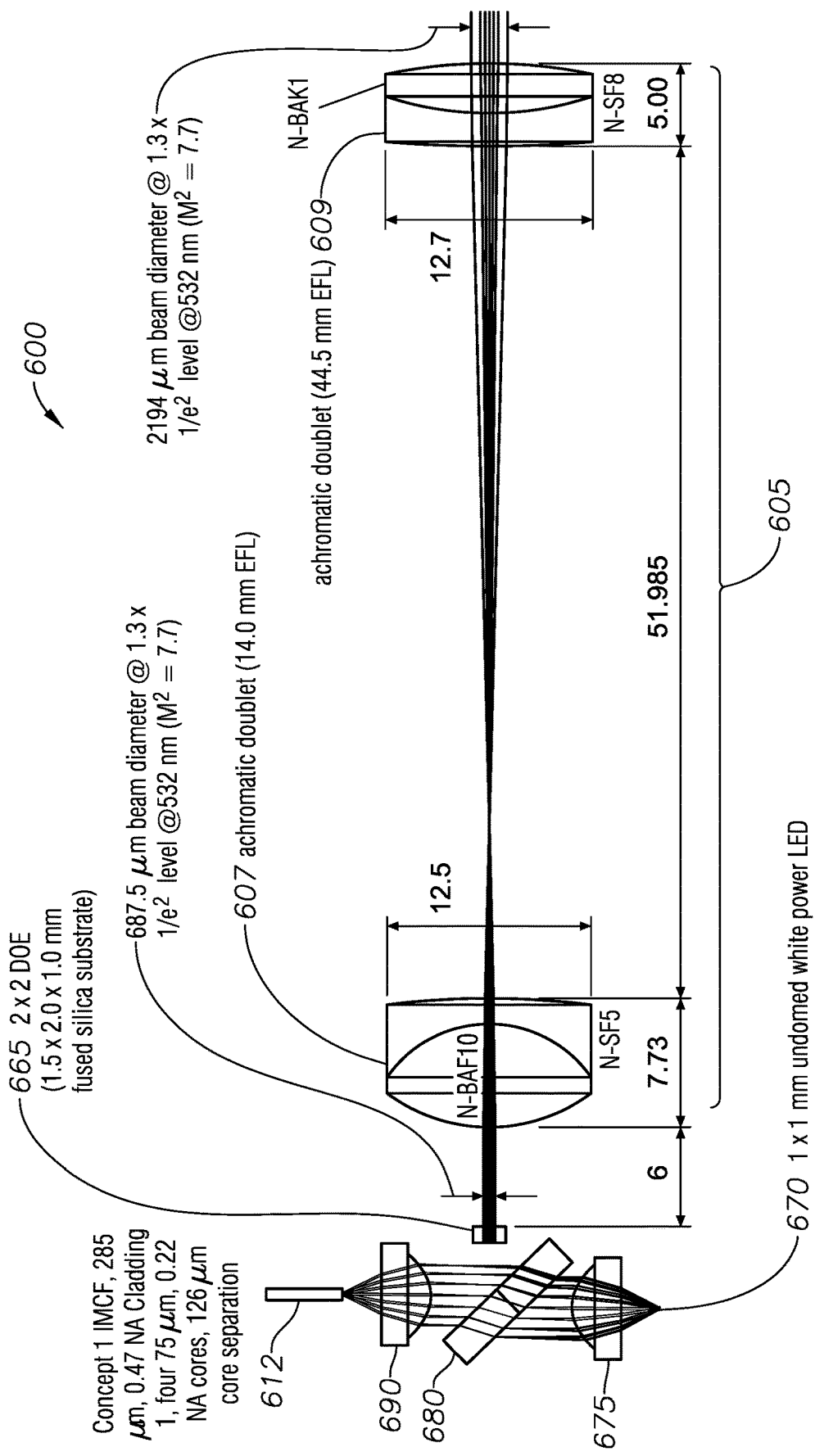
FIG. 6 illustrates a laser light multiplexing assembly in accordance with a particular embodiment of the present disclosure with a two-lens beam compressor for achieving correct collimated laser beam diameter for a diffraction optical element.

FIG. 6 illustrates a laser light multiplexing assembly 600 with a two-lens beam compressor 605 for achieving correct collimated laser beam diameter for a diffraction optical element (DOE) 665. The two-lens beam compressor 605 can include two achromatic doublets 607, 609 for focusing and then re-collimating the laser beams and for directing the collimated beams to the DOE 665 with an appropriate beam diameter. FIG. 6 includes precise dimensions for a specific embodiment; however, those with ordinary skill in the art having the benefit of the present disclosure will readily appreciate that other lens, dimensions, etc. can be used to achieve collimated laser beams having the appropriate lens diameter for other DOEs.

The laser light multiplexing assembly 600 also includes a collimating lens 675 for collimating or substantially collimating the illumination light from an illumination light source 670 and a beam splitter 680 that both: a) reflects the multi-spot pattern of laser aiming beams and treatment laser beams from the DOE 665 and b) transmits the illumination light (minus narrow bands of the spectrum corresponding with the laser aiming beam and the treatment laser beam) from the illumination light source 670. The laser light multiplexing assembly 600 further contains a condensing lens 690 arranged between the beam splitter 680 and a port 610 for coupling with a multi-core optical fiber cable 612 of an illuminated multi-spot laser probe assembly. The condensing lens 690 can be selected to precisely focus the multiplexed light onto an interface with a proximal end of the multi-core optical fiber cable 612.

Figure 7A:
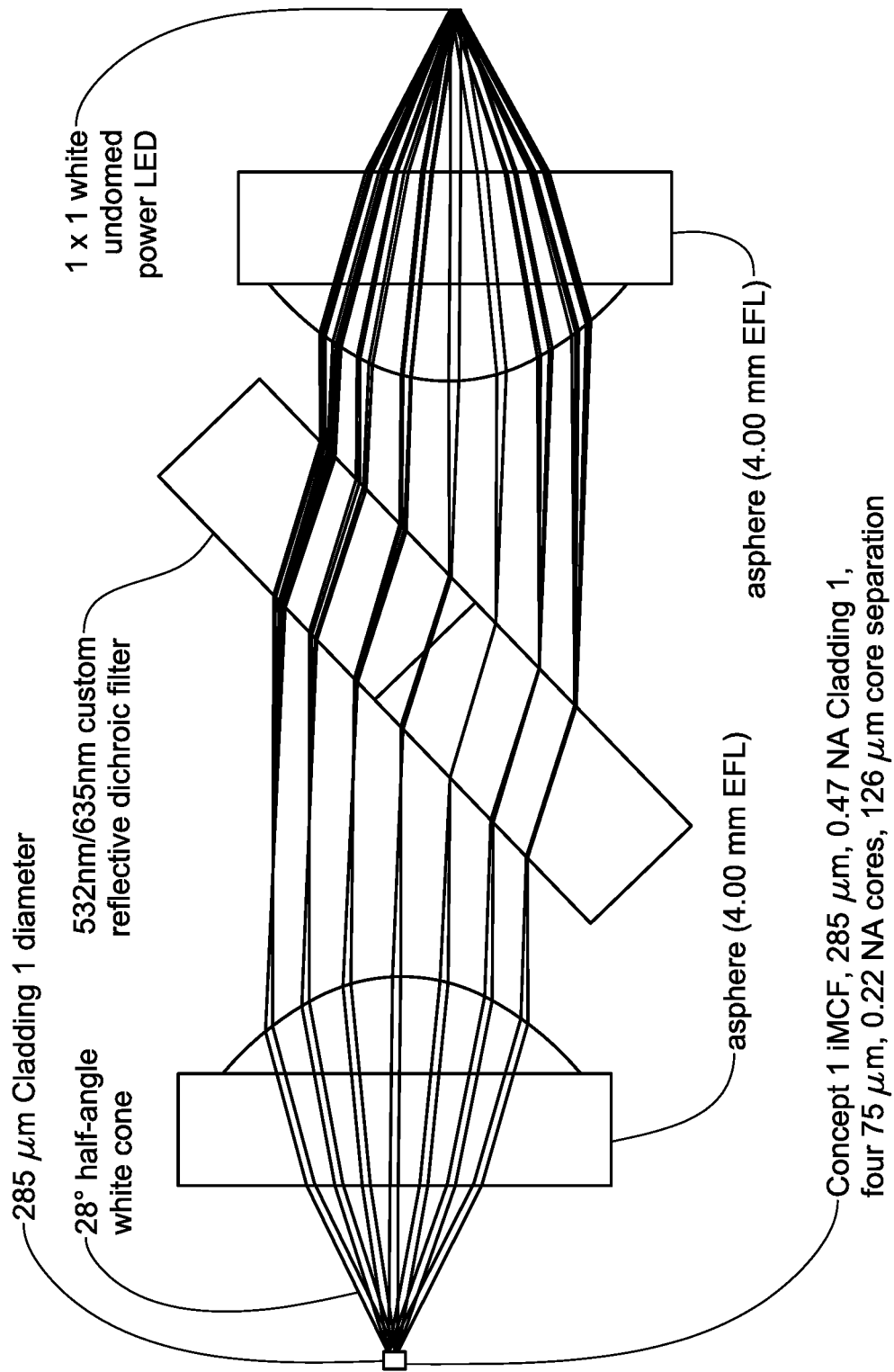
FIGS. 7A-7G illustrate examples of ray trace models of a multiplexing assembly in accordance with a particular embodiment of the present disclosure.
Figure 7B:
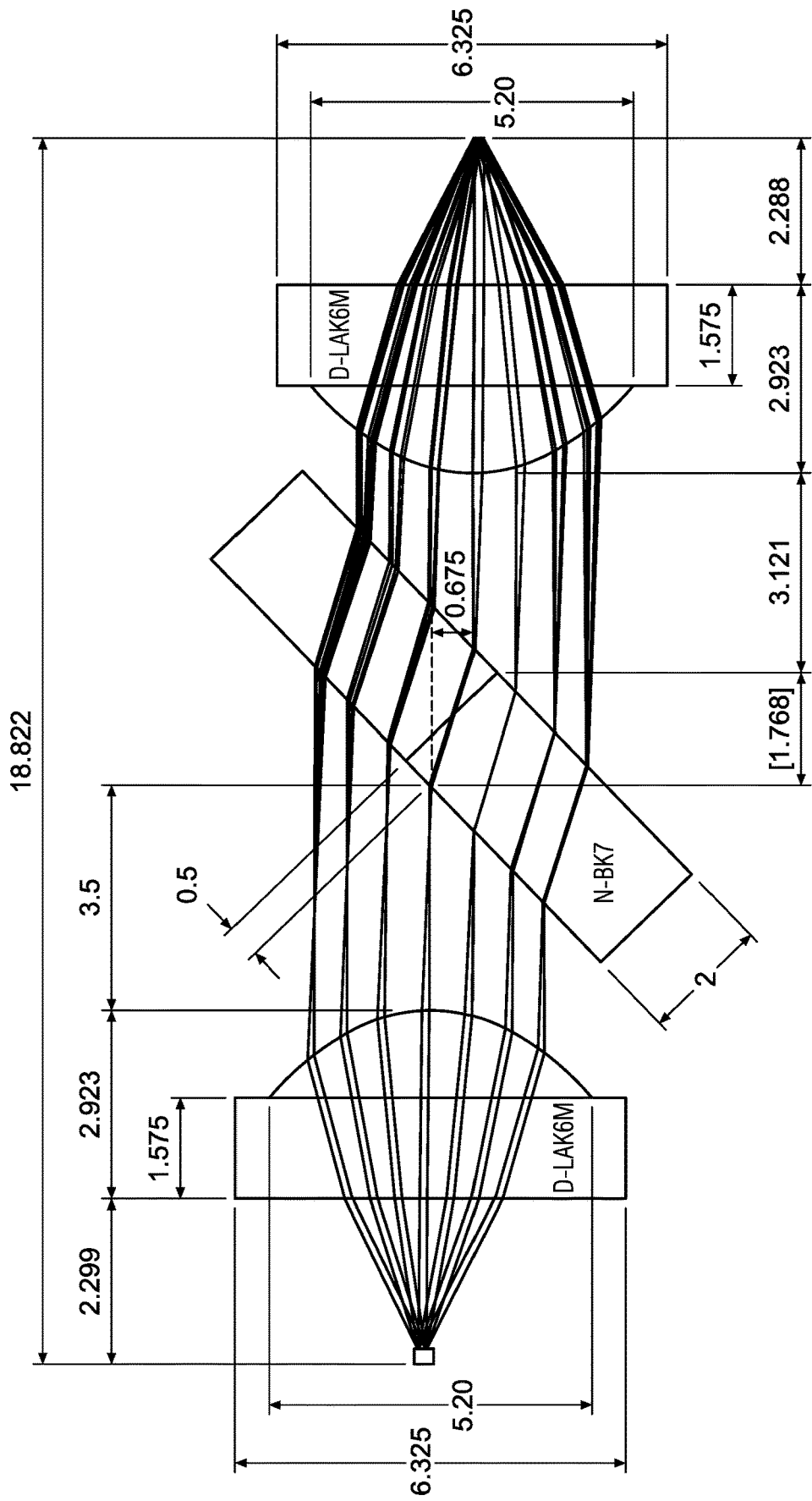
Figure 7C:
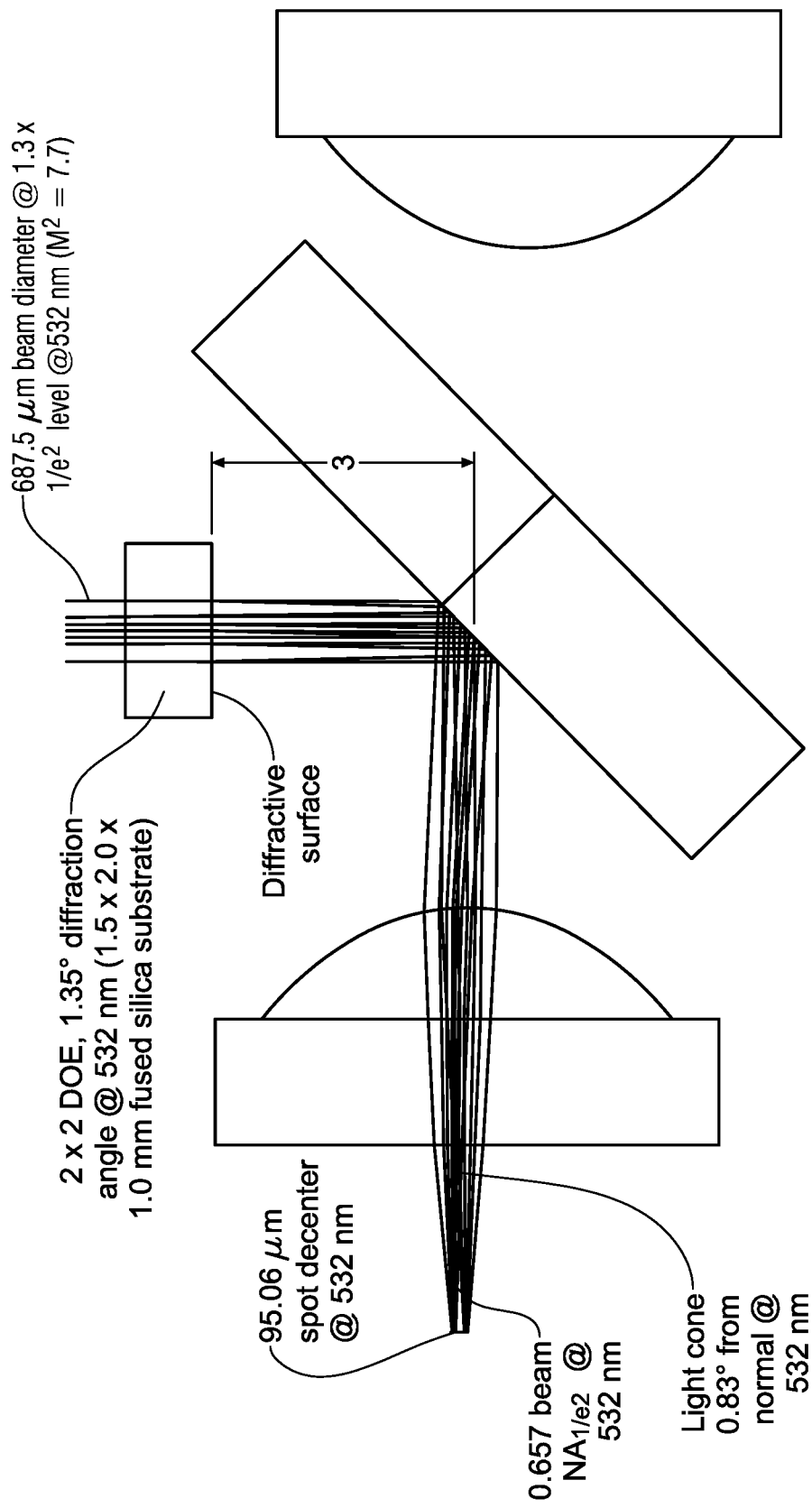
Figure 7D:
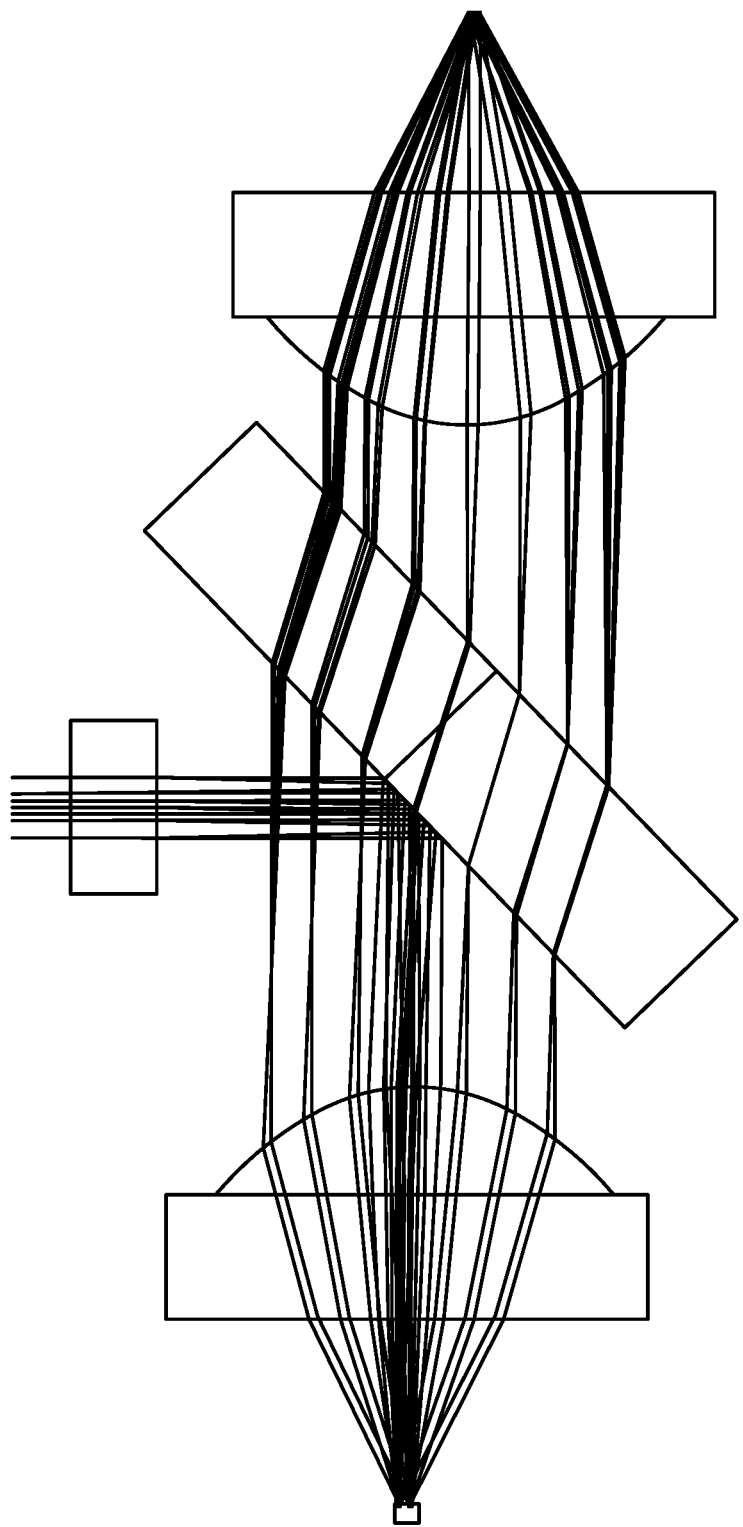
Figure 7E:
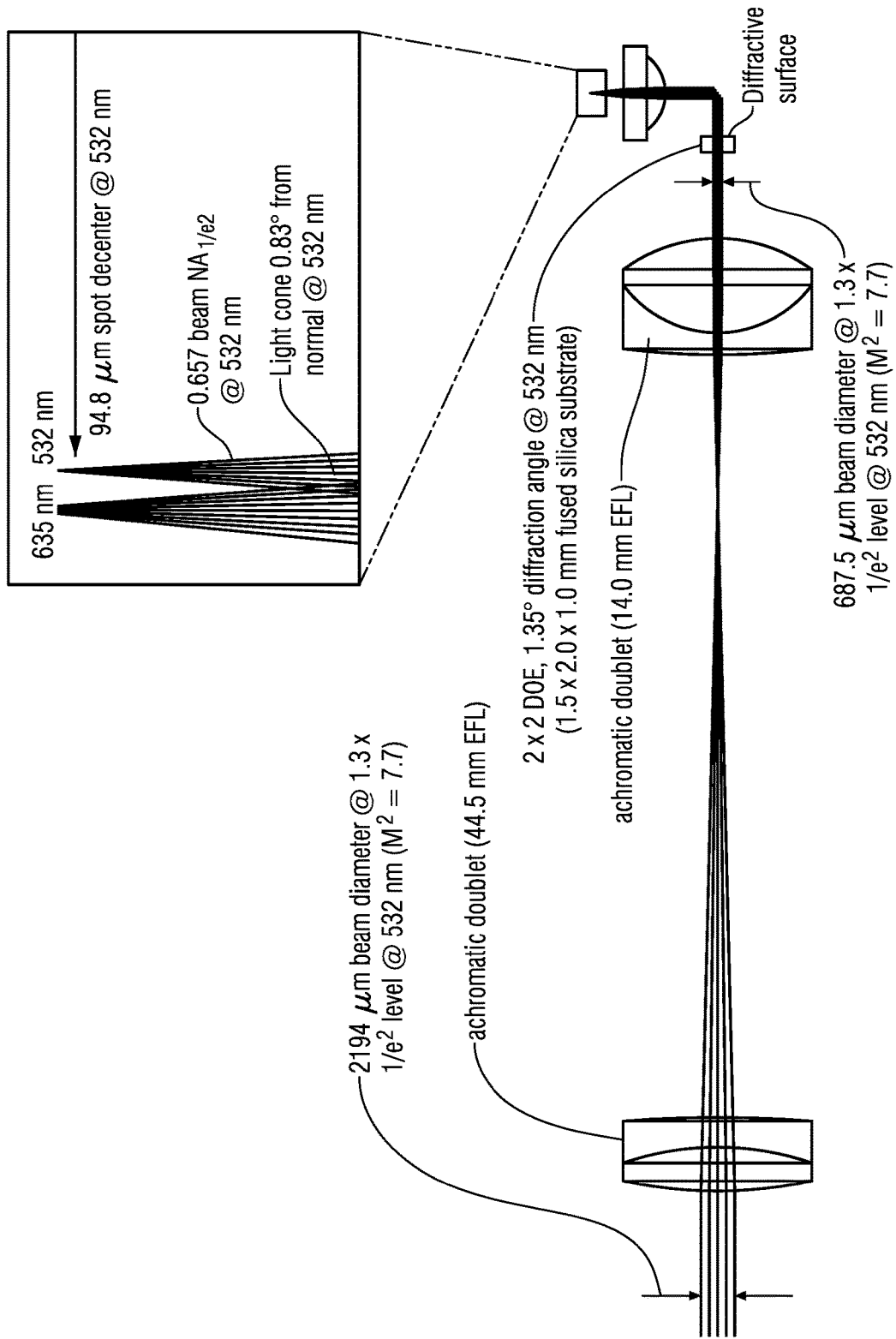
Figure 7F:
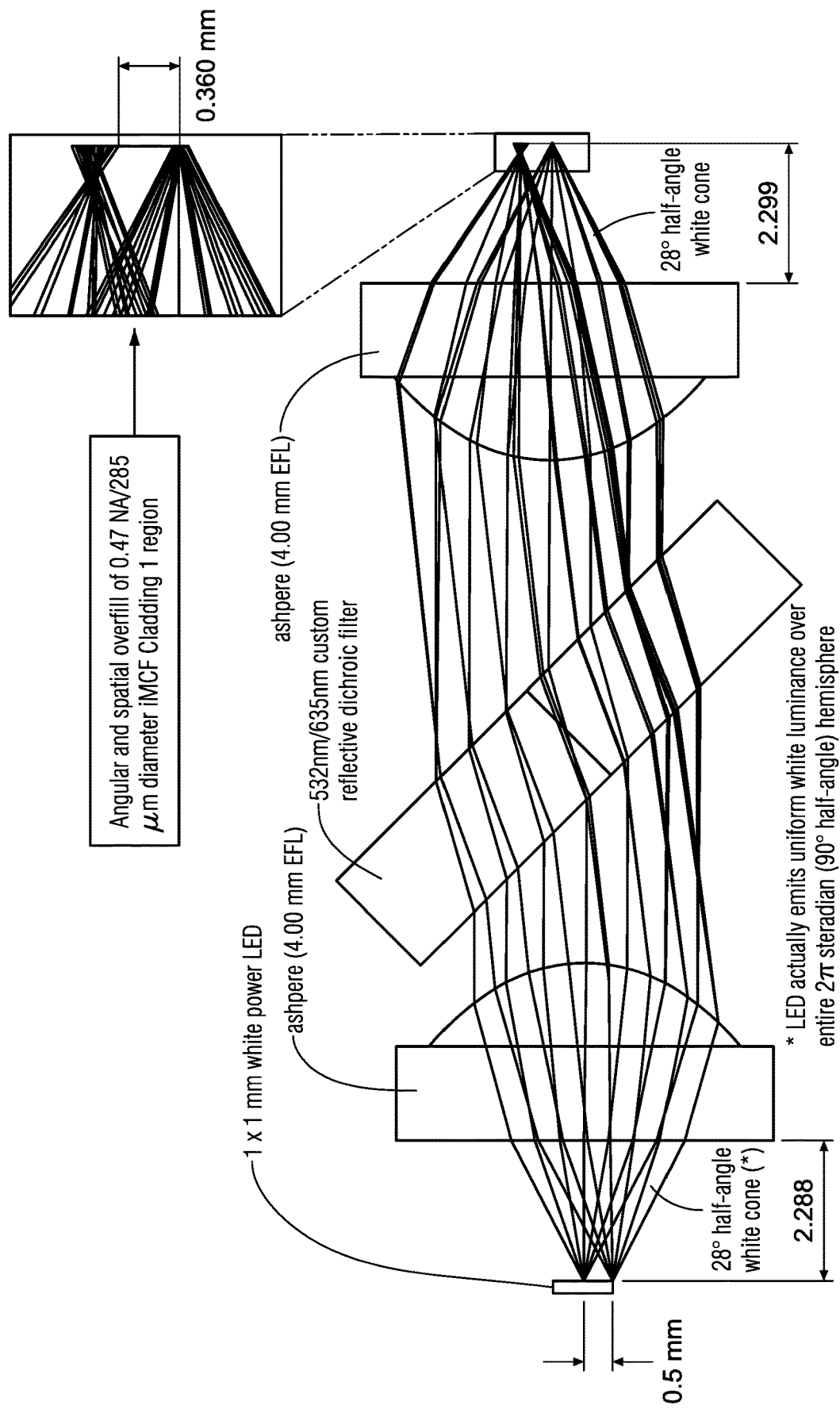
Figure 7G:
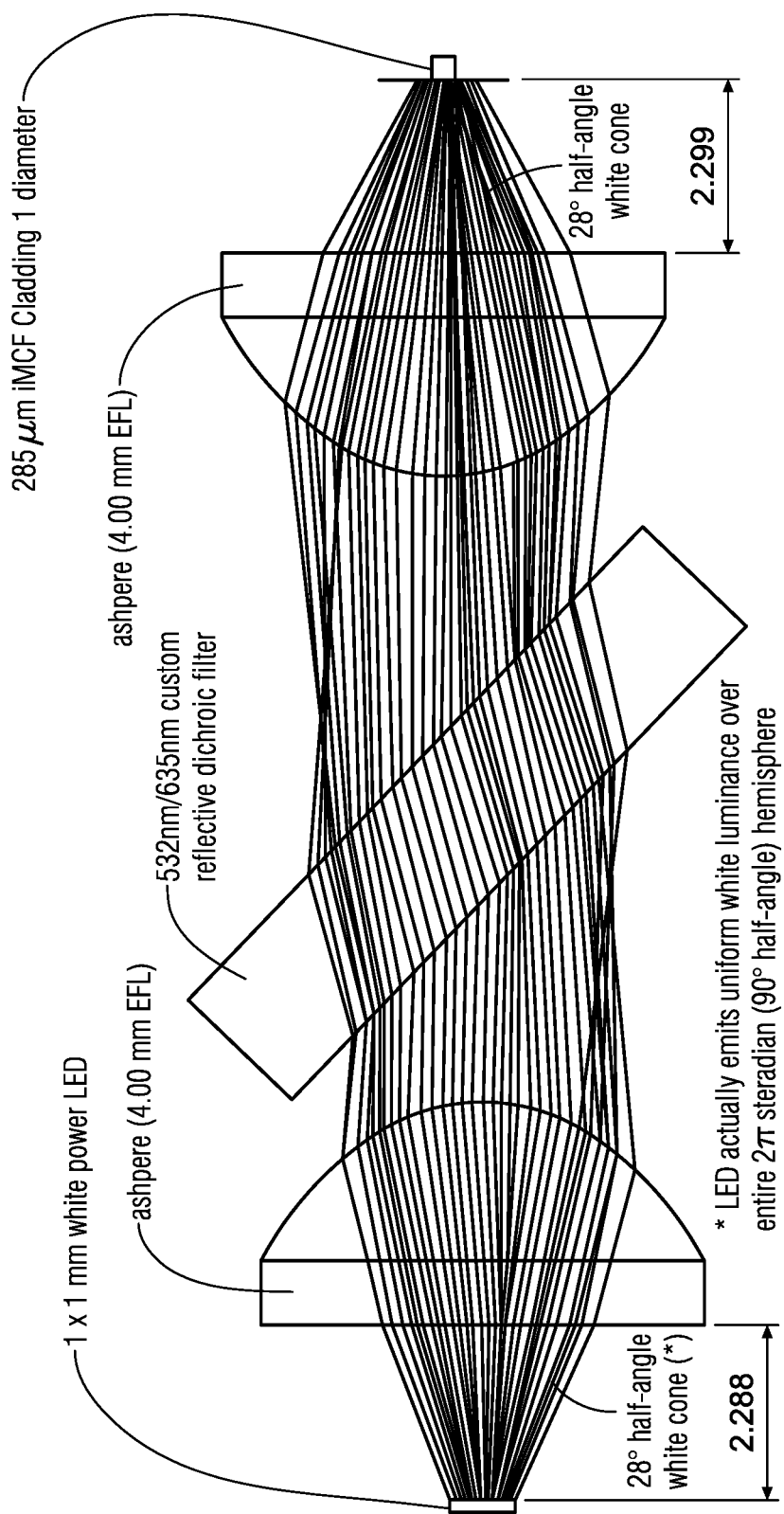

FIGS. 7A-7G illustrate examples of ray trace models of a multiplexing assembly according to some embodiments of the disclosed technology. FIGS. 7A-&B illustrates examples of a ray trace for white illumination light through a multiplexing assembly. FIG. 7C illustrates an example of a ray trace for laser treatment beams reflected from a beam splitter in a multiplexing assembly. FIG. 7D illustrates an example of a ray trace of white illumination light and laser treatment beams in a multiplexing assembly. FIG. 7E illustrates an example of a ray trace for laser treatment beams directed through a two-lens compressor, reflected from a beam splitter, and focused by a condensing lens. FIG. 7F-7G illustrate examples a ray trace for white illumination light through a multiplexing assembly.

The above-disclosed subject matter is to be considered illustrative, and not restrictive, and the appended claims are intended to cover all such modifications, enhancements, and

What is claimed is:

1. A laser system comprising:
a first port for coupling with a first laser probe assembly;
an additional port for coupling with an additional laser probe assembly;
the additional laser probe assembly;
a port selector;
a first beam splitter;
a second beam splitter;
a therapeutic laser source configured to direct a treatment laser beam to the port selector, the port selector configured to selectively and variably direct the treatment laser beam to the first beam splitter or the second beam splitter;
a first aiming laser source for directing a first aiming laser beam to the first beam splitter;
a second aiming laser source for directing a second aiming laser beam to the second beam splitter;
a diffractive optical element (DOE) configured to receive the treatment laser beam and the second aiming laser beam and to create a multi-spot laser pattern from the treatment laser beam and the second aiming laser beam;
an illumination system that emits white light;
a collimating lens that collimates the white light received from the illumination system into an illumination beam;
a condensing lens; and
a multiplexing beam splitter arranged to receive the illumination beam and the multi-spot laser pattern from the DOE, the multiplexing beam splitter configured to reflect the multi-spot laser pattern towards the condensing lens and to transmit the illumination beam from the collimating lens towards the condensing lens, thereby multiplexing the multi-spot laser pattern and the illumination beam,
wherein:
the first beam splitter directs the treatment laser beam and the first aiming laser beam to the first port, wherein the second beam splitter directs the treatment laser beam and the second aiming laser beam toward the additional port,
the condensing lens focuses a multiplexed beam of the illumination beam and the multi-spot laser pattern onto an interface in the additional port,
the additional laser probe assembly comprises a multi-core optical fiber cable with a proximal end which, when coupled with the additional port, abuts the interface in the additional port such that the focused, multiplexed multi-spot pattern and the illumination beam are focused on the proximal end of the multi-core optical fiber cable,
the multi-core optical fiber cable further comprises a first outer core surrounded by an outer-core cladding and a plurality of inner cores contained within the outer core, each inner core in the plurality of inner cores surrounded by an inner-core cladding, and
a refractive index of the outer core is greater than a refractive index of the outer-core cladding, wherein a refractive index of each of the inner cores in the plurality of inner cores is greater than a refractive index of the inner-core cladding.

2. The laser system of claim 1, further comprising:
a focusing lens arranged to receive the treatment laser beam and the first aiming laser beam from the first beam splitter and focus the treatment laser beam and the first aiming laser beam to the first port and onto an interface with an optical fiber of the first laser probe assembly.

3. The laser system of claim 1, further comprising:
a first beam detector, wherein the first beam splitter directs a portion of the treatment laser beam and the first aiming laser beam to the first beam detector.

4. The laser system of claim 3, further comprising:
an additional beam detector, wherein an additional beam splitter reflects a portion of the illumination beam to the additional beam detector.

5. The laser system of claim 1, further comprising:
a power monitor; and
a beam splitter arranged to receive the treatment laser beam from the therapeutic laser source and direct a portion of the treatment laser to the power monitor.

6. The laser system of claim 1, further comprising:
an optical element configured to transform a horizontally polarized treatment beam from the therapeutic laser source into a vertically polarized treatment beam.

7. The laser system of claim 6, wherein the optical element is selected from among a half-wave plate, a quartz-crystal polarization rotator, and a metamaterial polarization rotator.

8. The laser system of claim 1, further comprising:
a shutter arranged between the therapeutic laser source and the port selector, the shutter configured to alternatively block and transmit the treatment laser beam from reaching the port selector.

9. The laser system of claim 1, wherein the therapeutic laser source is configured to produce the treatment laser beam having a wavelength equal to 532 nm (nanometers), and wherein at least one of the first aiming laser source and the second aiming laser source is configured to produce a laser aiming beam having a wavelength equal to 635 nm.

10. The laser system of claim 1, wherein the DOE creates the multi-spot laser pattern in a 2×2 array pattern.

11. The laser system of claim 1, wherein the DOE contains a plurality of different diffraction regions selected for creating and transmitting various multi-spot patterns of laser light.

12. The laser system of claim 1, wherein the DOE comprises a movable linear stage with a plurality of diffraction regions for creating and transmitting multi-spot patterns of laser light.

13. The laser system of claim 1, wherein the additional laser probe assembly further comprises:
a handpiece with a probe tip coupled with a distal end of the multi-core optical fiber cable, the probe tip having a lens located at a distal end of the probe tip, wherein the distal end of the multi-core optical fiber cable terminates in an interface with the lens, and wherein the lens translates a geometry of the multiplexed multi-spot pattern and illumination beam from the distal end of the multi-core optical fiber cable onto a target surface.

14. The laser system of claim 13, wherein the refractive index of each of the inner cores in the plurality of inner cores is larger than the refractive index of the outer-core cladding.

15. The laser system of claim 13, wherein the plurality of inner cores contained within the outer core form a 2×2 array that matches a 2×2 multi-spot pattern from the DOE.

16. The laser system of claim 1, further comprising:
a beam compressor arranged between the therapeutic laser source and the DOE, the beam compressor configured to collimate the treatment laser beam to a diameter selected based on attributes of the DOE and a desired multi-spot pattern.

\* \* \* \* \*